United States Patent
Lee et al.

(10) Patent No.: US 9,951,136 B2
(45) Date of Patent: Apr. 24, 2018

(54) ANTI-IL-6 RECEPTOR ANTIBODIES AND METHODS OF USE

(71) Applicant: Apexigen, Inc., San Carlos, CA (US)

(72) Inventors: Sum Wai Pierre Lee, San Francisco, CA (US); Yaohuang Ke, San Francisco, CA (US); Yongke Zhang, Palo Alto, CA (US)

(73) Assignee: APEXIGEN, INC., San Carlos, CA (US)

( * ) Notice: Subject to any disclaimer, the term of this patent is extended or adjusted under 35 U.S.C. 154(b) by 75 days.

(21) Appl. No.: 14/268,932

(22) Filed: May 2, 2014

(65) Prior Publication Data

US 2014/0322239 A1   Oct. 30, 2014

Related U.S. Application Data

(63) Continuation of application No. 13/407,293, filed on Feb. 28, 2012, now Pat. No. 8,753,634.

(60) Provisional application No. 61/449,005, filed on Mar. 3, 2011.

(51) Int. Cl.
  C07K 16/30 (2006.01)
  C07K 16/28 (2006.01)

(52) U.S. Cl.
  CPC ...... C07K 16/2866 (2013.01); *C07K 2317/24* (2013.01); *C07K 2317/33* (2013.01); *C07K 2317/522* (2013.01); *C07K 2317/54* (2013.01); *C07K 2317/55* (2013.01); *C07K 2317/76* (2013.01); *C07K 2317/92* (2013.01)

(58) Field of Classification Search
  None
  See application file for complete search history.

(56) References Cited

U.S. PATENT DOCUMENTS

| | | | |
|---|---|---|---|
| 4,946,778 | A | 8/1990 | Ladner et al. |
| 5,091,513 | A | 2/1992 | Huston et al. |
| 5,132,405 | A | 7/1992 | Huston et al. |
| 5,675,063 | A | 10/1997 | Knight |
| 7,429,487 | B2 | 9/2008 | Pytela et al. |
| 7,462,697 | B2 | 12/2008 | Couto et al. |
| 7,803,371 | B2 | 9/2010 | Ke et al. |
| 8,753,634 | B2 | 6/2014 | Lee et al. |
| 2006/0165696 | A1 | 7/2006 | Okano et al. |
| 2006/0240012 | A1 | 10/2006 | Sugimura et al. |
| 2007/0134242 | A1 | 6/2007 | Nishimoto et al. |
| 2007/0280945 | A1 | 12/2007 | Stevens et al. |
| 2009/0297436 | A1 | 12/2009 | Garcia-Martinez et al. |
| 2010/0316636 | A1 | 12/2010 | Radin et al. |
| 2011/0098450 | A1 | 4/2011 | Igawa et al. |
| 2012/0034212 | A1 | 2/2012 | Bowen et al. |
| 2012/0128626 | A1 | 5/2012 | Smith |
| 2012/0225060 | A1 | 9/2012 | Lee et al. |
| 2012/0225069 | A1 | 9/2012 | Sheriff et al. |

FOREIGN PATENT DOCUMENTS

| | | |
|---|---|---|
| EP | 1690550 A1 | 8/2006 |
| EP | 1810980 A1 | 7/2007 |
| JP | 2009-539349 | 11/2009 |
| JP | 4555924 | 10/2010 |
| WO | WO 2005/037315 A1 | 4/2005 |
| WO | WO 2007/143168 A2 | 12/2007 |
| WO | WO 2009/140348 A2 | 11/2009 |
| WO | WO 2011/013786 A1 | 2/2011 |
| WO | WO 2012/118813 | 9/2012 |

OTHER PUBLICATIONS

Paul, Fundamental Immunology, 3rd Edition, 1993, pp. 292-295.*
Bendig M. M. (Methods: A Companion to Methods in Enzymology, 1995; 8:83-93).*
European Application No. 12752484.1, Extended European Search Report dated Aug. 7, 2014, 12 pages.
Bauer, J. et al., "Interleukin-6 in clinical medicine," Ann. Hematol., 62(6):203-210 (1991).
Brakenhoff, J. P. et al., "Structure-function analysis of human IL-6. Epitope mapping of neutralizing monoclonal antibodies with amino- and carboxyl-terminal deletion mutants," The Journal of Immunology, 145(2):561-568 (1990).
Campbell, I. L. et al., "Essential Role for Interferon-γ and Interleukin-6 in Autoimmune Insulin-dependent Diabetes in NOD/Wehi Mice," J. Clin. Invest., 87:739-742 (1991).
Coulie, P. G. et al., "High-affinity binding sites for human 26-kDa protein (interleukin 6, B cell stimulatory factor-2, human hybridoma plasmacytoma growth factor, interferon-β$_2$), different from those of type I interferon (α,β), on lymphoblastoid cells," Eur. J. Immunol., 17:1435-1440 (1987).
Gearing, D. P. et al., "The IL-6 Signal Transducer, gp130: an Oncostatin M Receptor and Affinity Converter for the LIF Receptor," Science 255:1434-1437 (1992).
Grau, G. E. et al., "Interleukin 6 Production in Experimental Cerebral Malaria: Modulation by Anticytokine Antibodies and Possible Role in Hypergammaglobulinemia," J.of Exp. Med., 172:1505-1508 (1990).
Grau, G. E., "Implications of cytokines in immunopathology: experimental and clinical data," Eur. Cytokine Net., 1(4):203-210 (1990).
Heinrich, P. C. et al., "Review Article: Interleukin-6 and the acute phase response," Biochem. J., 265:621-636 (1990).
Hibi, M. et al., "Molecular Cloning and Expression of an IL-6 Signal Transducer, gp130," Cell, 63:1149-1157 (1990).
Hirano, T. et al., "Biological and clinical aspects of interieukin 6," Immunology Today, 11:443-449 (1990).
Hirano, T. et al., "Excessive production of interleukin 6/B cell stimulatory factor-2 in rheumatoid arthritis," Eur. J. of Immunol., 18(11):1797-1801 (1988).

(Continued)

*Primary Examiner* — Michael Allen
(74) *Attorney, Agent, or Firm* — Cooley LLP

(57) ABSTRACT

The present invention provides anti-IL-6R monoclonal antibodies and related compositions, which may be used in any of a variety of therapeutic methods for the treatment of rheumatoid arthritis and other diseases.

17 Claims, 3 Drawing Sheets

(56) References Cited

OTHER PUBLICATIONS

Houssiau, F. et al., "Interleukin-6 in synovial fluid and serum of patients with rheumatoid arthritis and other inflammatory arthritides," Arthritis & Rheumatism, 31(6):784-788 (1988).
Jilka, R. L. et al., "Increased Osteoclast Development After Estrogen Loss: Mediation by Interleukin-6," Science, 257(5066):88-91 (1992).
Klein, B. et al., "Murine Anti-Interleukin-6 Monoclonal Antibody Therapy for a Patient With Plasma Cell Leukemia," Blood, 78(5):1198-1204 (1991).
Madhok, R. et al., "Serum interleukin 6 levels in rheumatoid arthritis: correlations with clinical and laboratory indices of disease activity," Annals of the Rheumatic Disease, 52:232-234 (1993).
Mihara, M. et al., "Humanized Antibody to Human Interleukin-6 Receptor Inhibits the Development of Collagen Arthritis in Cynomolgus Monkeys," Clinical Immunology, 98(3):319-326 (2001).
Roodman, G. D. et al., "Interleukin 6—A Potential Autocrine/Paracrine Factor in Paget's Disease of Bone," The Journal of Clinical Investigation, 89:46-52 (1992).
Sehgal, P. B., "Interleukin 6 in Infection and Cancer," Proc. Soc. Exp. Biol. Med., 195:183-191 (1990).
Starnes Jr., H. F. et al., "Anti-IL-6 monoclonal antibodies protect against lethal *Escherichia coli* infection and lethal tumor necrosis factor-α challenge in mice," Journal of Immunology, 145(12):4185-4191 (1990).
Strassmann, G. et al., "Evidence for the Involvement of Interleukin 6 in Experimental Cancer Cachexia," J. Clin. Invest., 89:1681-1684 (1992).
Taga, T. et al., "Interleukin-6 Triggers the Association of its Receptor with a Possible Signal Transducer, gp130," Cell, 58:573-581 (1989).
Taga, T. et al., "Receptors for B Cell Stimulatory Factor 2: Quantitation, Specficity, Distribution, and Regulation of Their Expression," J. of Exp.I Med., 166:967-981 (1987).
Takagi, N. et al., "Blockage of interleukin-6 receptor ameliorates joint disease in murine collagen-induced arthritis," Arthritis & Rheumatism, 41(12):2117-2121 (1998).
Uchiyama, Y, et al., "Tocilizumab, a Humanized Anti-interleukin-6 Receptor Antibody, Ameliorates Joints Swelling in Established Monkey Collagen-Induced Arthritis," Biol. Pharm. Bull., 31(6):1159-1163 (2008).
Van Snick, J., "Interieukin-6: an overview," Annu. Rev. Immunol., 8:253-278 (1990).
Yamasaki, K. et al., "Cloning and Expression of the Human Interleukin-6 (BSF-2/IFN beta 2) Receptor," Science, 241:825-828 (1988).
Rudikoff, et al., "Single amino acid substitution altering antigen-binding specificity," Proceedings of the National Academy of Sciences, 79: 1979-1983, 1982.
Panka, et al., "Variable region framework differences result in decreased or increased affinity of variant anti-digoxin ," Proceeding of the National Academy of Sciences, 85: 3080-3084, 1988.
Araki, M., et al., "Clinical improvement in a patient with neuromyelitis optica following therapy with the anti-IL-6 receptor monoclonal antibody tocilizumab." Mod. Rheumatol; 23(4):827-31; 2013.
Azevedo, A., et al., "IL-6/IL-6R as a potentiai key signaling pathway in prostate cancer development," World. J. Clin. Oncol. Dec. 10, 2011;2(12): 384-96.
Fragiadaki, K., et al., "Sleep disturbances and interleukin 6 receptor inhibition in rheumatoid arthritis," J. Rheumatol. Jan. 2012; 39(1): 60-2. Epub Dec. 1, 2011.
Galeotti, C., et al., "Sustained Remission of Multicentric Castleman Disease in Children Treated with Tocilizumab, an Anti-Interleukin-6 Receptor Antibody" Molecular Cancer Therapeutics; Aug. 11, 2012:1623-1626.
Jones, S.A., et al., "Therapeutic strategies for the clinical blockade of IL-6/gp130 signaling," J. Clin. Invest. Sep. 2011; 121(9): 3375-83. Epub Sep. 1, 2011.
Malíčková, K., et al., "Anti-inflammatory effect of biological treatment in patients with inflammatory bowel diseases: calprotectin and IL-6 changes do not correspond to sRAGE changes," Scand. J. Clin. Lab. Invest. Jul. 2010: 70(4) : 294-9.
Muhammad, K., et al., "Impact of IL-6 receptor inhibition on human memory B cells in vivo: impaired somatic hypermutation in preswitch memory B cells and modulation of mutational targeting in memory B cells," Ann. Rheum. Dis. Aug. 2011: 70(8) : 1507-10.
Murakami, M., et al., "The value of blocking IL-6 outside of rheumatoid arthritis: current perspective," Curr. Opin. Rheumatol. May 2011; 23(3): 273-7.
Nakahara, H., et al., "Anti-interleukin-6 receptor antibody therapy in rheumatic diseases," Endocr. Metab. Immune .Disord. Drug Targets. Dec. 2006: 6(4): 373-81.
Navarro-Millan, I., et al., "Systematic review of tocilizumab for rheumatoid arthritis: a new biologic agent targeting the interleukin-6 receptor" Clin Ther. Apr. 2012; 34(4):788-802.e3. Epub Mar. 22, 2012. Review.
Rethorst, C.D., et al., "Moderating effects of moderate-intensity physical activity in the relationship between depressive systems and interleukin-6 in primary care patients," Psychosom Med. Apr. 2011: 73(3) :265-269, Epub Mar. 1, 2011.
Roll, P., et al., "In vivo effects of the anti-interleukin-6 receptor inhibitor tocilizumab on the B cell compartment," Arthritis Rheum. May 2011; 63(5): 1255-64.
Smolen, J.S., et al., "Tocilizumab inhibits progression of joint damage in rheumatoid arthritis irrespective of its anti-inflammatory effects: disassociation of the link between inflammation and destruction." Ann. Rheum. Dis., May 2012: 71(5): 687-93.
Snir, A., et al.,"Anti-IL-6 receptor antibody (tocilizumab): a B cell targeting therapy," Clin. Exp. Rheumatol. Jul.-Aug. 2011; 29(4): 697-700, Epub Sep. 1, 2011.
Swerdlow, DI., et al., "The interleukin-6 receptor as a target for prevention of coronary heart disease: a mendelian randomisation analysis," Lancet. Mar. 31, 2012; 379(9822): 1214-24. Epub Mar. 14, 2012.
Tanaka, T., et al., "Immunotherapeutic implication of IL-6 blockade," Immunotherapy. Jan. 2012;4(1):87-105. Review.
Tanaka, T., et al., "Therapeutic targeting of the interleukin-6 receptor," Annual Review of Pharmacology and Toxicology vol. 52: Feb. 10, 2012: 199-219.
Van Rhee, F., et al. "Siltuximab, a novel anti-interleukin-6 monoclonal antibody, for Castleman's disease," J. Clin. Oncol. Aug. 10, 2010; 28(23): 3701-8. Epub Jul. 12, 2010.
International Search Report and Written Opinion for application No. PCT/US2012/026954, dated Sep. 24, 2012, 14 pages.
International Preliminary Report on Patentability for application No. PCT/US2012/026954, dated Sep. 3, 2013, 8 pages.

\* cited by examiner

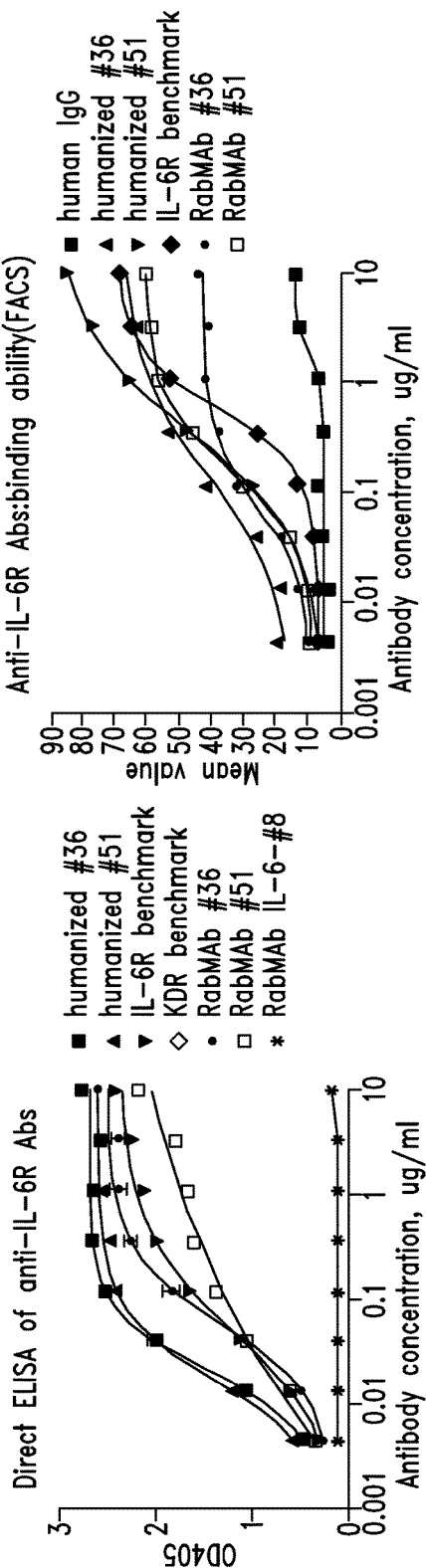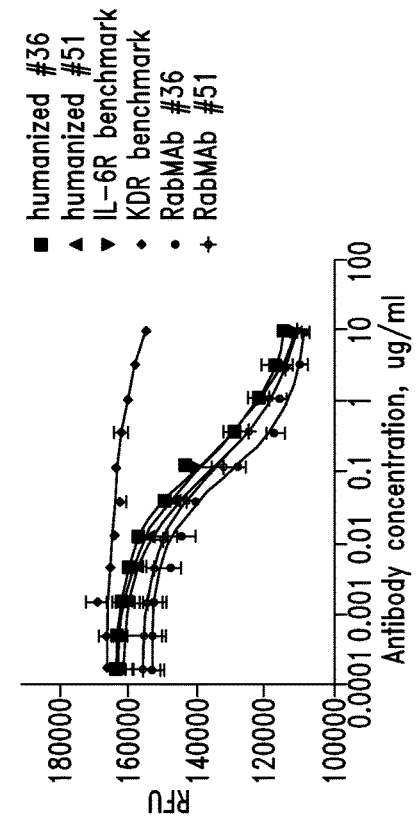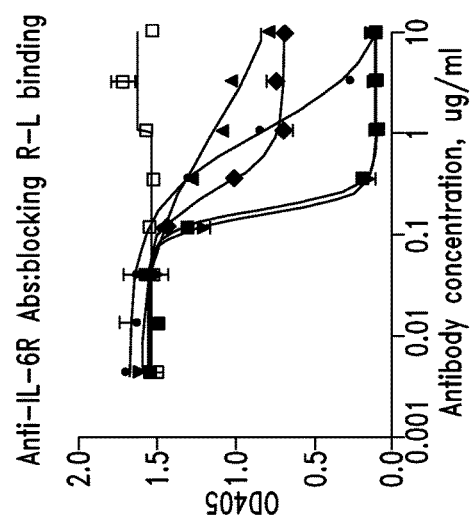

IL-6R antibody HC sequences

```
                                                              ===CDR1===
5   METGLRWLLLVAVLKGVQCQS-LEESGGRLVTPGTPLTLTCTVSGIDLSRYWMSWVRQAPGKGLEWI
21  METGLRWLLLVAVLKGVQCQS-VEESGGRLVTPGTPLTLTCTVSGIDLSNYYMSWVRQAPGKGLEWI
23  METGLRWLLLVAVLKGVQCQS-LEESGGRLVTPGTPLTLTCTVSGIDLSRYWMSWVRQAPGKGLEWI
36  METGLRWLLLVAVLKGVQCQS-VEESGGRLVTPGTPLTLTCTVSGFSLSSYYMSWVRQAPGKGLEWI
37  METGLRWLLLVAVLKGVQCQS-LEESGGRLVTPGTPLTLTCTVSGIDLSRYWMSWVRQAPGKGLEWI
40  METGLRWLLLVAVLKGVQCQS-LEESGGRLVSPGGSLTLTCTVSGVDLNTYAMGWVRQAPGKGLECI
42  METGLRWLLLVAVLKGVQCQS-VEESGGRLVTPGTPLTLTCTVSGFSLSNYWMSWVRQAPGKGLEWI
51  METGLRWLLLVAVLKGVQCQS-VEESGGRLVTPGTPLTLTCTASGFDISSYSLQWVRQSPGKGLEYI
R5  METGLRWLLLVAVLKGVQCQS-VEESGGRLVTPGTPLTVTCTASGFSLSTYWMSWVRQAPGKGLEWI
R15 METGLRWLLLVAVLKGVQCQS-LEESGGRLITPGGSLTLTCTVSGFSLTTYNVAWVRQAPGKGLEWI

======CDR2======                              =======CDR3=====
5   GMISG-GN-TWYASWAKGRFTISKTS-TTVDLKITSPTTEDTATYFCAR----GIDTGIATTFNLWGPGTLVTVSS
21  GISSTTSN-TFYASWAKGRFTISKTS-ATVDLKITSPTTEDTATYFCAR----YGGNSAYYAFSLWGQGTLVTVSS
23  GMISG-GN-TWYASWAKGRFTISKTS-TTVDLKITSPTTEDTATYFCAR----GIDTGIATTFNLWGPGTLVTVSS
36  GITTTSTN-TFYASWAKGRFTISKTS-ATVDLKITSPTIEDTATYFCAR----YGGNSAYYAFSLWGQGTLVTVSS
37  GMISG-GN-TWYASWAKGRFTISGTS-TTVDLKIISPTTADTATYFCAR----GIDTGIATTFNLWGPGTLVTVSS
40  GVILGSGT-TYYANWAKGRFTISKTSSTTVDLKMTNLTAADTATYFCAGDRYGSLEEVITPYFDLWGPGILVTVSS
42  AFIGG-GN-TFYASWAKGRFTISKTSSTTVDLSMPSPTTEDTATYFCARG---YGAPG----YDLWGQGTLVTVSL
51  GFIRPDGS-AHYATWAKGRFTISKTSSTTVDLKMTSLTTEDTATYFCAR-DDIS----SDYFPNLWGPGTLVTVSS
R5  GMIYGDSNNKFYANWAKGRFTISKTSSTTVDLKMTSLTTEDTATYFCAREYFADSXXGX--XFGIWGPGTLVTVSS
R15 GIIGG-TGNTHYTTWAKGRFTISKTS-TTVDLRITSPTTEDTATYFCAR---XXLGGGXDXDFDIWGPGTLVTVSS
```

*FIG. 2A*

IL-6R antibody LC sequences

```
                                                      ====CDR1=====
5    MDTRAPTQLLGLLLLWLPGATFA-QVLTQTPSSVSAAVGGTVTISCQSSQSVYNNNRLSWFQQKPGQPPKLL

21   MDTRAPTQLLGLLLLWLPGATFA-VVLTQTPSPVSAAVGGTVTINCQSSQSVYNNNYLAWYQQKPGQPPKLL

23   MDTRAATQLLGLLLLWLPGATFA-QVLTQTPSSVSTAVGGTVTISCQSSQNVYNNNRLSWFQQKPGQPPKLL

36   MDTRAPTQLLGLLLLWLPGATFA-QVLTQTASSVSAAVGGTVTISCQSSQSVYNNNYLAWFQQKPGQPPKLL

37   MDTRAPTQLLGLLLLWLPGATFA-QVLTQTPSSVSAAVGGTVTISCQSSQSVYSNNRLSWFQQKPGQPPKLL

40   MDTRAPTQLLGLLLLWLPGARCADVVMTQTPASVEAAVGGTVTIKCQASQNIYN--NLAWYQQKPAQPPKLL

42   MDTRAPTQLLGLLLLWLPGATFA-IVMTQTPSSKSVPVGDTVTINCQASESVYTNNRLSWYQQKPGQPPKLL

51   MDTRAPTQLLGLLLLWLPGATFA-QVLTQTPSPVSAAVGGTVTISCQASESVYNKNNLAWYQQKPGQPPKLL

R5   MDTRAPTQLLGLLLLWLPGATFA-QVLTQTPSPVSAAVGGTVTISCQSSQSVYKNNYLSWYQQKPGQPPKLL

R15  MDTRAPTQLLGLLLLWLPGARCA-YDMTQTPASVEVAVGGTVTIKCQASQNIRN--YLAWYQQKPGQRPKLL

=CDR2==                                 ======CDR3=====
5    IYYASTLASGVPSRFKGSGSGTQFTLTISDLECDDAATYYCQGYYS---GVI---NVFGGGTEVVVK

21   IYGASNLASGVPSRFKGSGSGTQFTLTISEVQCDDAATYYCQGYYN---GVI---FVFGGGTEVVVK

23   IYYTSTLPSGVPSRFKGSGSGTQFTLTISDLECDDAATYYCQGYYS---GVI---NVFGGGTEVVVK

36   IYGASNLASGVPSRFKGSGSGTQFTLTISDLECDNAATYYCQGYYN---GVI---FVFGGGTEVVVK

37   IYYTSTLASGVPSRFKGSGSGTQFTLTISDLECDDAATYYCQGYYS---GVI---NVFGGGTEVVVK

40   IYSASTLESGVPSRFKGSGSGTGYTLTISDLECADAATYYCQSA-YYTSYIDHN--VFGGGTEVVVE

42   IYYASTLASGVPSRFKGSGSGTQFTLTISDVVCDNAATYYCVGYKSSD-GDG---TAFGGGTEVVVK

51   IYDASDLASGVSSRFKGSGSGTQFTLTISDLECADAATYYCAGGGS---GNV---YDFGGGTEVVVK

R5   IYRASTLASGVSSRFKGSGSGTQFTLTISEVQCDDAATYVCQGYYS---GPI---YVFGGGTEVVVK

R15  IDAAANLASGVPSRFKGSGSGTEFTLTISDLECDDAATYYCQQG-YSVINVDN---IFGGGTEVVVK
```

*FIG. 2B*

ANTI-IL-6 RECEPTOR ANTIBODIES AND METHODS OF USE

CROSS REFERENCE TO RELATED APPLICATIONS

This application is a continuation of U.S. patent application Ser. No. 13/407,293 filed Feb. 28, 2012, now U.S. Pat. No. 8,753,634, which claims priority to U.S. Provisional Application No. 61/449,005 filed Mar. 3, 2011, which applications are incorporated by reference herein in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is APEX_012_02US_SEQUENCE_LISTING.txt. The text file is 53 KB, was created on May 2, 2014 and is being submitted electronically via EFS-Web.

BACKGROUND

Technical Field

The present invention relates generally to anti-IL-6 receptor (IL-6R) antibodies, compositions and methods of using same. The invention is more specifically related to anti-IL-6R antibodies and their manufacture and use. Such antibodies are useful, for example, in methods for treating any of a variety of inflammatory and oncological diseases.

Description of the Related Art

Interleukin-6 (IL-6) is a multi-functional cytokine that plays a central role in host defense mechanisms. Heinrich et al., Biochem. J. (1990) 26.5:621; Van Snick, J. Annu. Rev. Immunol. (1990) 8:253; and Himno et al., Immunol. Today (1990) 11:443. However, in a variety of human inflammatory, autoimmune, and neoplastic diseases, abnormal IL-6 production is observed and has been suggested to play a role in the pathogenesis of those diseases. Hirano et al., supra; Sehgal, P. B., Proc. Soc. Exp. Biol. Med. (1990) 195:183; Grau, G. E., Eur. Cytokine Net (1990) 1:203; Bauer et al., Ann. Hematol. (1991) 62:203; Campbell et al., J, Clin, Invest. (1991) 7:739; and Roodman et al., J. Clin. Invest. (1992) 89:46. Inhibitors of IL-6 bioactivity might thus be useful to study its role in disease and could have broad therapeutic applications.

IL-6 is produced by T cells, B cells, monocytes, fibroblasts, keratinocytes, endothelial cells, mesangial cells, and several tumor cell lines. IL-6 induces growth of T cells and differentiation of cytotoxic T cells by augmenting the expression of IL-2 receptor and the production of IL-2. IL-6 acts synergistically with IL-3 to support the formation of multilineage blast cell colonies in hematopoiesis and induces differentiation of macrophages, megakaryocytes, and osteoclasts. In the acute-phase reaction, IL-6 stimulates hepatocytes to produce acute-phase proteins such as C-reactive protein (CRP), fibrinogen, al-antitrypsin and serum amyloid A. IL-6 also causes leukocytosis and fever when administered in vivo and also acts as a growth factor for renal mesangial cells, epidermal keratinocytes, and various types of tumor cells, for example, in plasmacytoma, multiple myeloma, and renal cell carcinoma.

IL-6 overproduction is involved in sepsis (Starnes, Jr., H. F. et al., J. Immunol. (1990) 145:4185), and is also implicated in multiple myeloma, or plasma cell leukemia (Klein, B. et al., Blood (1991) 78:1198). Other diseases include bone resorption (osteoporosis) (Roodman, G. D. et al., J., Clin. Invest. (1992) 89:46; Jilka, R. L. et al., Science (1992) 257:88-91), cachexia (Strassman, G. et al., J. Clin. Invest. (1992) 89:1681), psoriasis, systemic-onset juvenile idiopathic arthritis, systemic lupus erythematosus, mesangial proliferative glomerulonephritis, renal cell carcinoma, Kaposi's sarcoma, rheumatoid arthritis (Eur. J. Immunol. 18, 1797-1801, 1988; Arthritis Rheum. 31, 784-788, 1988; Ann. Rheum. Dis. 52, 232-234, 1993), hyper gammaglobulinemia (Grau, G. E. et al., J. Exp. Meal. (1990) 172:1505), Castleman's disease, IgM gammopathy, cardiac myxoma and autoimmune insulin-dependent diabetes (Campbell, I. L. et al., J, Clin, Invest., (1991) 87:739). Rat anti-mouse IL-6R antibody prevented the development of collagen-induced arthritis (CIA) in DBA/1J mice and anti-human IL-6 antibody was effective in both prevention and treatment of a monkey CIA model. This evidence suggest that IL-6 plays an essential role in the pathogenesis of arthritis and support the utility of these animal models for the study of arthritis and the therapeutic efficacy of anti-IL-6 or IL-6R treatments (Arthritis Rheum. 41, 2117-2121, 1998; Clin Immunol. 2001 March; 98(3):319-26; Biol Pharm Bull. 2008 June; 31(6): 1159-63).

IL-6 functions through interaction with at least two specific receptors on the surface of target cells. Taga et al., J. Exp. Med. (1987) 166:967; and Coulie et al., Eur. J. Immunol, (1987) 17:1435. The cDNAs for these two receptor chains have been cloned, and they code for two transmembrane glycoproteins: the 80 kDa IL-6 receptor "IL-6R") and a 130 kDa glycoprotein called "gp130". Yamasaki et al., Science (1988) 241:825; and Hibi et al., Cell (1990) 63:1149. IL-6 interacts with these glycoproteins following a unique mechanism. First, IL-6R binds to IL-6 with low affinity (Kd=about 1 nM) without triggering a signal. Taga et al., Cell (1989) 58:573. The IL-6/IL-6R complex subsequently associates with gp130, which transduces the signal. Hibi et al., supra; and Taga et al., supra. Gp130 itself has no affinity for IL-6 in solution, but stabilizes the IL-6/IL-6R complex on the membrane, resulting in high affinity binding of IL-6 (Kd=about 10 pM). Hibi et al., supra. It was recently found that gp130 is also a low affinity receptor for oncostatin M and an affinity converter for the LIF receptor (Gearing, D. P. et al., Science (1992) 255:1434).

One method for neutralization of IL-6 activity is the use of antibodies that specifically bind to IL-6. Neutralizing monoclonal antibodies (MAbs) to IL-6 can be divided in two groups, based on the recognition of two distinct epitopes on the IL-6 molecule, designated Site I and Site II. Site I is a conformational epitope composed of both amino terminal and carboxy terminal portions of the IL-6 molecule, and Site II includes critical amino acids. Brakenhoff et al. (1990, J. Immunol. 145:561-568).

Another way to neutralize IL-6 activity is to inhibit the ligand-receptor interactions by binding to and blocking IL-6R. This invention provides these and other advantages as described further herein.

BRIEF SUMMARY

One aspect of the present disclosure provides an isolated antibody, or an antigen-binding fragment thereof, that binds to human IL-6R, comprising (i) a heavy chain variable region comprising a VHCDR1 region identical to the amino acid residues of SEQ ID NO:3, a VHCDR2 region identical to the amino acid residues of SEQ ID NO:4, and a VHCDR3 region identical to the amino acid residues of SEQ ID NO:5; and (ii) a light chain variable region comprising a VLCDR1 region identical to the amino acid residues of SEQ ID NO:6, a VLCDR2 region identical to the amino acid residues of SEQ ID NO:7, and a VLCDR3 region identical to the amino acid residues set forth in SEQ ID NO: 8; or a variant of said antibody, or an antigen-binding fragment thereof, comprising heavy and light chain variable regions identical to the heavy and light chain variable regions of (i) and (ii) except for up to 8 amino acid substitutions in said CDR regions. In one embodiment the heavy chain variable region comprises the amino acid sequence set forth in SEQ ID NO:1. In another embodiment of this aspect of the disclosure, the light chain variable region comprises the amino acid sequence set forth in SEQ ID NO:2.

Another aspect of the present disclosure provides an isolated antibody, or an antigen-binding fragment thereof, that binds to human IL-6R, comprising a heavy chain variable region comprising the amino acid sequence set forth in SEQ ID NO:1. In one embodiment, the antibody comprises a light chain variable region which comprises an amino acid sequence having at least 90% identity to the amino acid sequence set forth in SEQ ID NO:2. In another embodiment, the antibody comprises a light chain variable region which comprises the amino acid sequence set forth in SEQ ID NO:2.

Another aspect of the disclosure provides an isolated antibody, or an antigen-binding fragment thereof, that binds to human IL-6R, comprising a light chain variable region comprising the amino acid sequence set forth in SEQ ID NO:2. In one embodiment of this aspect, the antibody comprises a heavy chain variable region which comprises an amino acid sequence having at least 90% identity to the amino acid sequence set forth in SEQ ID NO:1.

A further aspect of the disclosure provides an isolated antibody, or an antigen-binding fragment thereof, that binds to human IL-6R, comprising (i) a heavy chain variable region comprising a VHCDR1 region identical to the amino acid residues of SEQ ID NO:13, a VHCDR2 region identical to the amino acid residues of SEQ ID NO:14, and a VHCDR3 region identical to the amino acid residues of SEQ ID NO:15; and (ii) a light chain variable region comprising a VLCDR1 region identical to the amino acid residues of SEQ ID NO:16, a VLCDR2 region identical to the amino acid residues of SEQ ID NO:17, and a VLCDR3 region identical to the amino acid residues set forth in SEQ ID NO:18; or a variant of said antibody, or an antigen-binding fragment thereof, comprising heavy and light chain variable regions identical to the heavy and light chain variable regions of (i) and (ii) except for up to 8 amino acid substitutions in said CDR regions. In one embodiment of this aspect of the disclosure, the heavy chain variable region comprises the amino acid sequence set forth in SEQ ID NO:11. In a further embodiment of this aspect of the disclosure, the light chain variable region comprises the amino acid sequence set forth in SEQ ID NO:12.

Yet another aspect of the disclosure provides an isolated antibody, or an antigen-binding fragment thereof, that binds to human IL-6R, comprising a heavy chain variable region comprising the amino acid sequence set forth in SEQ ID NO:11. In one embodiment the antibody comprises a light chain variable region which comprises an amino acid sequence having at least 90% identity to the amino acid sequence set forth in 12. In a further embodiment, the antibody comprises a light chain variable region which comprises the amino acid sequence set forth in SEQ ID NO:12.

Another aspect of the disclosure provides an isolated antibody, or an antigen-binding fragment thereof, that binds to human IL-6R, comprising a light chain variable region comprising the amino acid sequence set forth in SEQ ID NO:12. In one embodiment, the isolated antibody, or antigen binding fragment thereof, comprises a heavy chain variable region which comprises an amino acid sequence having at least 90% identity to the amino acid sequence set forth in SEQ ID NO:10.

In further aspects of the disclosure, the isolated antibodies described herein are humanized. In one particular embodiment, the humanized antibody comprises a VH region comprising the amino acid sequence set forth in SEQ ID NO:9 and a VL region comprising the amino acid sequence set forth in SEQ ID NO:10. In a further embodiment, the humanized antibody of this disclosure comprises a VH region comprising the amino acid sequence set forth in SEQ ID NO:19 and a VL region comprising the amino acid sequence set forth in SEQ ID NO:20.

In certain embodiments of the disclosure, the isolated antibodies disclosed herein are selected from the group consisting of a single chain antibody, a ScFv, a univalent antibody lacking a hinge region, and a minibody. In certain embodiments, the antibody is a Fab, a Fab' fragment, a F(ab')$_2$ fragment, or a whole antibody. In further embodiments, the antibodies described herein comprise a human IgG constant domain, and in certain particular embodiments, the IgG constant domain comprises an IgG1 CH1 domain. In one embodiment, the IgG constant domain comprises an IgG1 Fc region.

Another aspect of the present disclosure provides an isolated antibody, or an antigen-binding fragment thereof, that competes with the antibodies described herein for binding to human IL-6R.

One aspect of this disclosure provides an isolated antibody, or antigen-binding fragment thereof, that binds IL-6R with a KD of 1.3 nM or lower.

A further aspect of this disclosure provides an isolated antibody, or antigen-binding fragment thereof, that binds IL-6R with a $K_D$ of 0.5 nM or lower.

In another embodiment of the isolated antibodies or antigen-binding fragments thereof as described herein, the isolated antibody or antigen-binding fragment thereof, blocks IL-6 binding to IL-6R, inhibits IL-6R signaling, inhibits one or more IL6 or IL-6R-mediated biological functions or inhibits STAT 3 phosphorylation, or a combination of one or more of the aforementioned. In another embodiment of any of the antibodies described herein the one or more IL6 or IL-6R mediated biological functions includes but is not limited to IL-6 induced cell proliferation, IL-6 induced cell differentiation, and IL-6 induced production of CRP, fibrinogen and serum amyloid A.

Another aspect of this disclosure provides an isolated polynucleotide encoding an isolated antibody, or antigen-binding fragment thereof as described herein.

Yet a further aspect of the disclosure provides a composition comprising a physiologically acceptable carrier and a therapeutically effective amount of an isolated antibody or antigen-binding fragment thereof as described herein.

An additional aspect of this disclosure provides a method for treating an inflammatory disease, such as rheumatoid arthritis, comprising administering to a patient having the inflammatory disease, a composition comprising a physiologically acceptable carrier and a therapeutically effective amount of an isolated antibody or antigen-binding fragment thereof as described herein, thereby treating the patient having the inflammatory disease. In another embodiment, the inflammatory disease is juvenile idiopathic arthritis Another aspect of this disclosure provides a method for treating Castleman's disease, comprising administering to a patient having Castleman's disease a composition comprising a physiologically acceptable carrier and a therapeutically effective amount of an isolated antibody or antigen-binding fragment thereof as described herein, thereby treating the Castleman's disease.

Yet another aspect of this disclosure provides a method for treating systemic lupus erythematosus, comprising administering to a patient having systemic lupus erythematosus a composition comprising a physiologically acceptable carrier and a therapeutically effective amount of an isolated antibody or antigen-binding fragment thereof as described herein, thereby treating the systemic lupus erythematosus.

An additional aspect of this disclosure provides a method for treating a cancer associated with aberrant IL-6 expression, comprising administering to a patient having such a cancer a composition comprising a physiologically acceptable carrier and a therapeutically effective amount of an isolated antibody or antigen-binding fragment thereof as described herein, thereby treating the cancer associated with aberrant IL-6 expression. In one embodiment, the cancer is multiple myeloma.

A further aspect of the present disclosure provides a method for treating cancer-related fatigue or cachexia, comprising administering to a patient having cancer-related fatigue or cachexia a composition comprising a physiologically acceptable carrier and a therapeutically effective amount of an isolated antibody or antigen-binding fragment thereof as described herein, thereby treating the cancer-related fatigue or cachexia.

BRIEF DESCRIPTION OF THE SEVERAL VIEWS OF THE DRAWINGS

FIG. 1A-FIG. 1D: Humanized lead anti-IL-6R antibody candidates retain most activities of their rabbit counterparts. Panel A: Direct ELISA of anti-IL-6R antibodies; Panel B: Anti-IL-6R antibody binding to IL-6R on human myeloma U266B1 cells measured by FACS; Panel C: Ability of anti-IL-6R antibodies to block IL-6 binding to IL-6R; Panel D: Humanized anti-IL-6R antibodies inhibit IL-6 mediated proliferation of TF-1 cells.

FIG. 2A and FIG. 2B show an amino acid alignment of the VH (2A) and VL (2B) regions of 10 anti-IL6R rabbit antibodies identified as described in Example 1 and summarized in Table 1. The amino acid sequences for the VH regions are provided in SEQ ID NOs:25-34 (FIG. 2A, top to bottom) and VL regions are provided in SEQ ID NOs: 35-44 (FIG. 2B, top to bottom). The CDRs are shown by underlining. The VHCDR1 amino acid sequences are provided in SEQ ID NOs:45-54 (FIG. 2A, top to bottom), the VHCDR2 amino acid sequences are provided in SEQ ID NOs:55-64 (FIG. 2A, top to bottom) and the VHCDR3 amino acid sequences are provided in SEQ ID NOs:65-74 (FIG. 2A, top to bottom). The VLCDR1 amino acid sequences are provided in SEQ ID NOs:75-84 (FIG. 2B, top to bottom), the VLCDR2 amino acid sequences are provided in SEQ ID NOs:85-94 (FIG. 2B, top to bottom) and the VLCDR3 amino acid sequences are provided in SEQ ID Nos:75-104 (FIG. 2B, top to bottom). The VHCDR1, VHCDR2, VHCDR3, VLCDR1, VLCDR2, and VLCDR3 amino acid sequences of clone 36 and clone 51 are also provided in SEQ ID NOs:3-8 and 13-18, respectively.

BRIEF DESCRIPTION OF THE SEQUENCES

SEQ ID NO:1 is the amino acid sequence of the VH region of the clone 36 rabbit anti-IL-6R antibody.

SEQ ID NO:2 is the amino acid sequence of the VL region of the clone 36 rabbit anti-IL-6R antibody.

SEQ ID NO:3 is the amino acid sequence of the VHCDR1 region of the clone 36 rabbit anti-IL-6R antibody.

SEQ ID NO:4 is the amino acid sequence of the VHCDR2 region of the clone 36 rabbit anti-IL-6R antibody.

SEQ ID NO:5 is the amino acid sequence of the VHCDR3 region of the clone 36 rabbit anti-IL-6R antibody.

SEQ ID NO:6 is the amino acid sequence of the VLCDR1 region of the clone 36 rabbit anti-IL-6R antibody.

SEQ ID NO:7 is the amino acid sequence of the VLCDR2 region of the clone 36 rabbit anti-IL-6R antibody.

SEQ ID NO:8 is the amino acid sequence of the VLCDR3 region of the clone 36 rabbit anti-IL-6R antibody.

SEQ ID NO:9 is the amino acid sequence of the humanized sequence of the VH region of the clone 36 rabbit anti-IL-6R antibody.

SEQ ID NO:10 is the amino acid sequence of the humanized sequence of the VL region of the clone 36 rabbit anti-IL-6R antibody.

SEQ ID NO:11 is the amino acid sequence of the VH region of the clone 51 rabbit anti-IL-6R antibody.

SEQ ID NO:12 is the amino acid sequence of the VL region of the clone 51 rabbit anti-IL-6R antibody.

SEQ ID NO:13 is the amino acid sequence of the VHCDR1 region of the clone 51 rabbit anti-IL-6R antibody.

SEQ ID NO:14 is the amino acid sequence of the VHCDR2 region of the clone 51 rabbit anti-IL-6R antibody.

SEQ ID NO:15 is the amino acid sequence of the VHCDR3 region of the clone 51 rabbit anti-IL-6R antibody.

SEQ ID NO:16 is the amino acid sequence of the VLCDR1 region of the clone 51 rabbit anti-IL-6R antibody.

SEQ ID NO:17 is the amino acid sequence of the VLCDR2 region of the clone 51 rabbit anti-IL-6R antibody.

SEQ ID NO:18 is the amino acid sequence of the VLCDR3 region of the clone 51 rabbit anti-IL-6R antibody.

SEQ ID NO:19 is the amino acid sequence of the humanized sequence of the VH region of the clone 51 rabbit anti-IL-6R antibody.

SEQ ID NO:20 is the amino acid sequence of the humanized sequence of the VL region of the clone 51 rabbit anti-IL-6R antibody.

SEQ ID NO:21: is the amino acid sequence of human IgG1 constant region which includes CH1, hinge, CH2 and CH3 domains.

SEQ ID NO:22: is the polynucleotide sequence encoding the amino acid sequence of human IgG1 constant region as set forth in SEQ ID NO:21.

SEQ ID NO:23: is the amino acid sequence of human Ck constant region.

SEQ ID NO:24: is the polynucleotide sequence encoding the amino acid sequence of human Ck constant region as set forth in SEQ ID NO:23.

SEQ ID NO:25 is the amino acid sequence of the VH region of the clone 5 rabbit anti-IL-6R antibody as shown in FIG. 2.

SEQ ID NO:26 is the amino acid sequence of the VH region of the clone 21 rabbit anti-IL-6R antibody as shown in FIG. 2.

SEQ ID NO:27 is the amino acid sequence of the VH region of the clone 23 rabbit anti-IL-6R antibody as shown in FIG. 2.

SEQ ID NO:28 is the amino acid sequence of the VH region of the clone 36 rabbit anti-IL-6R antibody as shown in FIG. 2.

SEQ ID NO: 29 is the amino acid sequence of the VH region of the clone 37 rabbit anti-IL-6R antibody as shown in FIG. 2.

SEQ ID NO: 30 is the amino acid sequence of the VH region of the clone 40 rabbit anti-IL-6R antibody as shown in FIG. 2.

SEQ ID NO: 31 is the amino acid sequence of the VH region of the clone 42 rabbit anti-IL-6R antibody as shown in FIG. 2.

SEQ ID NO: 32 is the amino acid sequence of the VH region of the clone 51 rabbit anti-IL-6R antibody as shown in FIG. 2.

SEQ ID NO: 33 is the amino acid sequence of the VH region of the clone R5 rabbit anti-IL-6R antibody as shown in FIG. 2.

SEQ ID NO: 34 is the amino acid sequence of the VH region of the clone R15 rabbit anti-IL-6R antibody as shown in FIG. 2.

SEQ ID NO: 35 is the amino acid sequence of the VL region of the clone 5 rabbit anti-IL-6R antibody as shown in FIG. 2.

SEQ ID NO: 36 is the amino acid sequence of the VL region of the clone 21 rabbit anti-IL-6R antibody as shown in FIG. 2.

SEQ ID NO: 37 is the amino acid sequence of the VL region of the clone 23 rabbit anti-IL-6R antibody as shown in FIG. 2.

SEQ ID NO: 38 is the amino acid sequence of the VL region of the clone 36 rabbit anti-IL-6R antibody as shown in FIG. 2.

SEQ ID NO: 39 is the amino acid sequence of the VL region of the clone 37 rabbit anti-IL-6R antibody as shown in FIG. 2.

SEQ ID NO: 40 is the amino acid sequence of the VL region of the clone 40 rabbit anti-IL-6R antibody as shown in FIG. 2.

SEQ ID NO: 41 is the amino acid sequence of the VL region of the clone 42 rabbit anti-IL-6R antibody as shown in FIG. 2.

SEQ ID NO: 42 is the amino acid sequence of the VL region of the clone 51 rabbit anti-IL-6R antibody as shown in FIG. 2.

SEQ ID NO: 43 is the amino acid sequence of the VL region of the clone R5 rabbit anti-IL-6R antibody as shown in FIG. 2.

SEQ ID NO: 44 is the amino acid sequence of the VL region of the clone R15 rabbit anti-IL-6R antibody as shown in FIG. 2.

SEQ ID NO:45 is the amino acid sequence of the VHCDR1 of the clone 5 rabbit anti-IL-6R antibody as shown in FIG. 2.

SEQ ID NO:46 is the amino acid sequence of the VHCDR1 of the clone 21 rabbit anti-IL-6R antibody as shown in FIG. 2.

SEQ ID NO: 47 is the amino acid sequence of the VHCDR1 of the clone 23 rabbit anti-IL-6R antibody as shown in FIG. 2.

SEQ ID NO: 48 is the amino acid sequence of the VHCDR1 of the clone 36 rabbit anti-IL-6R antibody as shown in FIG. 2.

SEQ ID NO: 49 is the amino acid sequence of the VHCDR1 of the clone 37 rabbit anti-IL-6R antibody as shown in FIG. 2.

SEQ ID NO: 50 is the amino acid sequence of the VHCDR1 of the clone 40 rabbit anti-IL-6R antibody as shown in FIG. 2.

SEQ ID NO: 51 is the amino acid sequence of the VHCDR1 of the clone 42 rabbit anti-IL-6R antibody as shown in FIG. 2.

SEQ ID NO: 52 is the amino acid sequence of the VHCDR1 of the clone 51 rabbit anti-IL-6R antibody as shown in FIG. 2.

SEQ ID NO: 53 is the amino acid sequence of the VHCDR1 of the clone R5 rabbit anti-IL-6R antibody as shown in FIG. 2.

SEQ ID NO: 54 is the amino acid sequence of the VHCDR1 of the clone R15 rabbit anti-IL-6R antibody as shown in FIG. 2.

SEQ ID NO: 55 is the amino acid sequence of the VHCDR2 of the clone 5 rabbit anti-IL-6R antibody as shown in FIG. 2.

SEQ ID NO: 56 is the amino acid sequence of the VHCDR2 of the clone 21 rabbit anti-IL-6R antibody as shown in FIG. 2.

SEQ ID NO: 57 is the amino acid sequence of the VHCDR2 of the clone 23 rabbit anti-IL-6R antibody as shown in FIG. 2.

SEQ ID NO: 58 is the amino acid sequence of the VHCDR2 of the clone 36 rabbit anti-IL-6R antibody as shown in FIG. 2.

SEQ ID NO: 59 is the amino acid sequence of the VHCDR2 of the clone 37 rabbit anti-IL-6R antibody as shown in FIG. 2.

SEQ ID NO: 60 is the amino acid sequence of the VHCDR2 of the clone 40 rabbit anti-IL-6R antibody as shown in FIG. 2.

SEQ ID NO: 61 is the amino acid sequence of the VHCDR2 of the clone 42 rabbit anti-IL-6R antibody as shown in FIG. 2.

SEQ ID NO: 62 is the amino acid sequence of the VHCDR2 of the clone 51 rabbit anti-IL-6R antibody as shown in FIG. 2.

SEQ ID NO: 63 is the amino acid sequence of the VHCDR2 of the clone R5 rabbit anti-IL-6R antibody as shown in FIG. 2.

SEQ ID NO: 64 is the amino acid sequence of the VHCDR2 of the clone R15 rabbit anti-IL-6R antibody as shown in FIG. 2.

SEQ ID NO: 65 is the amino acid sequence of the VHCDR3 of the clone 5 rabbit anti-IL-6R antibody as shown in FIG. 2.

SEQ ID NO: 66 is the amino acid sequence of the VHCDR3 of the clone 21 rabbit anti-IL-6R antibody as shown in FIG. 2.

SEQ ID NO: 67 is the amino acid sequence of the VHCDR3 of the clone 23 rabbit anti-IL-6R antibody as shown in FIG. 2.

SEQ ID NO: 68 is the amino acid sequence of the VHCDR3 of the clone 36 rabbit anti-IL-6R antibody as shown in FIG. 2.

SEQ ID NO: 69 is the amino acid sequence of the VHCDR3 of the clone 37 rabbit anti-IL-6R antibody as shown in FIG. 2.

SEQ ID NO: 70 is the amino acid sequence of the VHCDR3 of the clone 40 rabbit anti-IL-6R antibody as shown in FIG. 2.

SEQ ID NO: 71 is the amino acid sequence of the VHCDR3 of the clone 42 rabbit anti-IL-6R antibody as shown in FIG. 2.

SEQ ID NO: 72 is the amino acid sequence of the VHCDR3 of the clone 51 rabbit anti-IL-6R antibody as shown in FIG. 2.

SEQ ID NO: 73 is the amino acid sequence of the VHCDR3 of the clone R5 rabbit anti-IL-6R antibody as shown in FIG. 2.

SEQ ID NO: 74 is the amino acid sequence of the VHCDR3 of the clone R15 rabbit anti-IL-6R antibody as shown in FIG. 2.

SEQ ID NO: 75 is the amino acid sequence of the VLCDR1 of the clone 5 rabbit anti-IL-6R antibody as shown in FIG. 2.

SEQ ID NO: 76 is the amino acid sequence of the VLCDR1 of the clone 21 rabbit anti-IL-6R antibody as shown in FIG. 2.

SEQ ID NO: 77 is the amino acid sequence of the VLCDR1 of the clone 23 rabbit anti-IL-6R antibody as shown in FIG. 2.

SEQ ID NO: 78 is the amino acid sequence of the VLCDR1 of the clone 36 rabbit anti-IL-6R antibody as shown in FIG. 2.

SEQ ID NO: 79 is the amino acid sequence of the VLCDR1 of the clone 37 rabbit anti-IL-6R antibody as shown in FIG. 2.

SEQ ID NO: 80 is the amino acid sequence of the VLCDR1 of the clone 40 rabbit anti-IL-6R antibody as shown in FIG. 2.

SEQ ID NO: 81 is the amino acid sequence of the VLCDR1 of the clone 42 rabbit anti-IL-6R antibody as shown in FIG. 2.

SEQ ID NO: 82 is the amino acid sequence of the VLCDR1 of the clone 51 rabbit anti-IL-6R antibody as shown in FIG. 2.

SEQ ID NO: 83 is the amino acid sequence of the VLCDR1 of the clone R5 rabbit anti-IL-6R antibody as shown in FIG. 2.

SEQ ID NO: 84 is the amino acid sequence of the VLCDR1 of the clone R15 rabbit anti-IL-6R antibody as shown in FIG. 2.

SEQ ID NO: 85 is the amino acid sequence of the VLCDR2 of the clone 5 rabbit anti-IL-6R antibody as shown in FIG. 2.

SEQ ID NO: 86 is the amino acid sequence of the VLCDR2 of the clone 21 rabbit anti-IL-6R antibody as shown in FIG. 2.

SEQ ID NO: 87 is the amino acid sequence of the VLCDR2 of the clone 23 rabbit anti-IL-6R antibody as shown in FIG. 2.

SEQ ID NO: 88 is the amino acid sequence of the VLCDR2 of the clone 36 rabbit anti-IL-6R antibody as shown in FIG. 2.

SEQ ID NO: 89 is the amino acid sequence of the VLCDR2 of the clone 37 rabbit anti-IL-6R antibody as shown in FIG. 2.

SEQ ID NO: 90 is the amino acid sequence of the VLCDR2 of the clone 40 rabbit anti-IL-6R antibody as shown in FIG. 2.

SEQ ID NO: 91 is the amino acid sequence of the VLCDR2 of the clone 42 rabbit anti-IL-6R antibody as shown in FIG. 2.

SEQ ID NO: 92 is the amino acid sequence of the VLCDR2 of the clone 51 rabbit anti-IL-6R antibody as shown in FIG. 2.

SEQ ID NO: 93 is the amino acid sequence of the VLCDR2 of the clone R5 rabbit anti-IL-6R antibody as shown in FIG. 2.

SEQ ID NO: 94 is the amino acid sequence of the VLCDR2 of the clone R15 rabbit anti-IL-6R antibody as shown in FIG. 2.

SEQ ID NO: 95 is the amino acid sequence of the VLCDR3 of the clone 5 rabbit anti-IL-6R antibody as shown in FIG. 2.

SEQ ID NO: 96 is the amino acid sequence of the VLCDR3 of the clone 21 rabbit anti-IL-6R antibody as shown in FIG. 2.

SEQ ID NO: 97 is the amino acid sequence of the VLCDR3 of the clone 23 rabbit anti-IL-6R antibody as shown in FIG. 2.

SEQ ID NO: 98 is the amino acid sequence of the VLCDR3 of the clone 36 rabbit anti-IL-6R antibody as shown in FIG. 2.

SEQ ID NO: 99 is the amino acid sequence of the VLCDR3 of the clone 37 rabbit anti-IL-6R antibody as shown in FIG. 2.

SEQ ID NO: 100 is the amino acid sequence of the VLCDR3 of the clone 40 rabbit anti-IL-6R antibody as shown in FIG. 2.

SEQ ID NO: 101 is the amino acid sequence of the VLCDR3 of the clone 42 rabbit anti-IL-6R antibody as shown in FIG. 2.

SEQ ID NO: 102 is the amino acid sequence of the VLCDR3 of the clone 51 rabbit anti-IL-6R antibody as shown in FIG. 2.

SEQ ID NO: 103 is the amino acid sequence of the VLCDR3 of the clone R5 rabbit anti-IL-6R antibody as shown in FIG. 2.

SEQ ID NO: 104 is the amino acid sequence of the VLCDR3 of the clone R15 rabbit anti-IL-6R antibody as shown in FIG. 2.

SEQ ID NOs:105 and 106 are illustrative linker amino acid sequences.

SEQ ID NO:107 is an illustrative flexible polylinker amino acid sequence.

DETAILED DESCRIPTION

The present disclosure relates to antibodies and antigen-binding fragments thereof the specifically bind to IL-6R, in particular antibodies having specific epitopic specificity and functional properties. One embodiment of the invention encompasses specific humanized antibodies and fragments thereof capable of binding to IL-6R, blocking IL-6R binding with IL-6 and inhibiting IL-6 induced downstream cell signaling and biological effects. In more specific embodiments of the invention, the antibodies described herein specifically bind to IL-6R with affinity of about 199 picomolar and block IL-6R binding to IL-6.

Embodiments of the invention pertain to the use of anti-IL-6R antibodies or antigen-binding fragments thereof for the diagnosis, assessment and treatment of diseases and disorders associated with IL-6 or aberrant expression thereof. The subject antibodies are used in the treatment or prevention of rheumatoid arthritis, multiple sclerosis, Castleman's disease, and plasmacytoma/multiple myeloma, among other diseases.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Molecular Biology* or *Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); Oligonucleotide Synthesis (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

Embodiments of the present invention relate to antibodies that bind to the IL-6 receptor (IL-6R). In particular, the antibodies described herein specifically bind to IL-6R with unexpectedly high affinity, block IL-6 binding to the IL-6R, block IL-6 activity and have therapeutic utility for the treatment of diseases associated with aberrant expression IL-6. The antibodies described herein also have advantageous properties such as the ability to inhibit a variety of IL-6-mediated biological effects (e.g., STAT3 phosphorylation and downstream signaling events, Ras-Raf intracellular signaling, IL-6 induced cell proliferation, IL-6 induced cell differentiation, IL-6 induced production of CRP, fibrinogen, serum amyloid A, and other IL-6 mediated effects known to the skilled person). The antibodies described herein may also have effects on IL-6R receptor internalization.

Sequences of illustrative antibodies, or antigen-binding fragments, or complementarity determining regions (CDRs) thereof, are set forth in SEQ ID NOs:1-20 and 25-104.

As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule. As used herein, the term encompasses not only intact polyclonal or monoclonal antibodies, but also fragments thereof (such as dAb, Fab, Fab', F(ab')$_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. "Diabodies", multivalent or multispecific fragments constructed by gene fusion (WO94/13804; P. Holliger et al., Proc. Natl. Acad. Sci. USA 90 6444-6448, 1993) are also a particular form of antibody contemplated herein. Minibodies comprising a scFv joined to a CH3 domain are also included herein (S. Hu et al., Cancer Res., 56, 3055-3061, 1996). See e.g., Ward, E. S. et al., Nature 341, 544-546 (1989); Bird et al., Science, 242, 423-426, 1988; Huston et al., PNAS USA, 85, 5879-5883, 1988); PCT/US92/09965; WO94/13804; P. Holliger et al., Proc. Natl. Acad. Sci. USA 90 6444-6448, 1993; Y. Reiter et al., Nature Biotech, 14, 1239-1245, 1996; S. Hu et al., Cancer Res., 56, 3055-3061, 1996.

The term "antigen-binding fragment" as used herein refers to a polypeptide fragment that contains at least one CDR of an immunoglobulin heavy and/or light chains that binds to the antigen of interest, in particular to the IL-6 receptor. In this regard, an antigen-binding fragment of the herein described antibodies may comprise 1, 2, 3, 4, 5, or all 6 CDRs of a VH and VL sequence set forth herein from antibodies that bind IL-6R. An antigen-binding fragment of the IL-6R-specific antibodies described herein is capable of binding to IL-6R. In certain embodiments, an antigen-binding fragment or an antibody comprising an antigen-binding fragment, prevents or inhibits IL-6 binding to the IL-6R and subsequent signaling events. In certain embodiments, the antigen-binding fragment binds specifically to and/or inhibits or modulates the biological activity of human IL-6R.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, an antibody is said to specifically bind an antigen when it preferentially recognizes its target antigen in a complex mixture of proteins and/or macromolecules. An antibody is said to specifically bind an antigen when the equilibrium dissociation constant is $\leq 10^{-7}$ or $10^{-8}$ M. In some embodiments, the equilibrium dissociation constant may be $\leq 10^{-9}$ M or $\leq 10^{-10}$ M.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof, now available on the Internet (immuno.bme.nwu.edu).

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

In certain embodiments, single chain Fv or scFV antibodies are contemplated. For example, Kappa bodies (Ill et al., Prot. Eng. 10: 949-57 (1997); minibodies (Martin et al., EMBO J 13: 5305-9 (1994); diabodies (Holliger et al., PNAS 90: 6444-8 (1993); or Janusins (Traunecker et al., EMBO J 10: 3655-59 (1991) and Traunecker et al., Int. J. Cancer Suppl. 7: 51-52 (1992), may be prepared using standard molecular biology techniques following the teachings of the present application with regard to selecting antibodies having the desired specificity. In still other embodiments, bispecific or chimeric antibodies may be made that encompass the ligands of the present disclosure. For example, a chimeric antibody may comprise CDRs and framework regions from different antibodies, while bispecific antibodies may be generated that bind specifically to IL-6R through one binding domain and to a second molecule through a second binding domain. These antibodies may be produced through recombinant molecular biological techniques or may be physically conjugated together.

A single chain Fv (sFv) polypeptide is a covalently linked $V_H$::$V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, an IL-6R binding antibody as described herein is in the form of a diabody. Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

A dAb fragment of an antibody consists of a VH domain (Ward, E. S. et al., Nature 341, 544-546 (1989)).

Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (J. B. B. Ridgeway et al., *Protein Eng.*, 9, 616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This proprietary antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The small size of the UniBody® can be a great benefit when treating some forms of cancer, allowing for better distribution of the molecule over larger solid tumors and potentially increasing efficacy.

In certain embodiments, the antibodies of the present disclosure may take the form of a nanobody. Nanobodies are encoded by single genes and are efficiently produced in almost all prokaryotic and eukaryotic hosts e.g. *E. coli* (see e.g. U.S. Pat. No. 6,765,087), molds (for example *Aspergillus* or *Trichoderma*) and yeast (for example *Saccharomyces, Kluyvermyces, Hansenula* or *Pichia* (see e.g. U.S. Pat. No. 6,838,254). The production process is scalable and multi-kilogram quantities of nanobodies have been produced. Nanobodies may be formulated as a ready-to-use solution having a long shelf life. The Nanoclone method (see, e.g., WO 06/079372) is a proprietary method for generating Nanobodies against a desired target, based on automated high-throughput selection of B-cells.

In certain embodiments, the anti-IL-6R antibodies or antigen-binding fragments thereof as disclosed herein are humanized. This refers to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio, A. F. et al., (1989) *Proc Natl Acad Sci USA* 86:4220-4224; Queen et al., *PNAS* (1988) 86:10029-10033; Riechmann et al., *Nature* (1988) 332:323-327). Illustrative methods for humanization of the anti-IL-6R antibodies disclosed herein include the methods described in U.S. Pat. No. 7,462,697. Illustrative humanized antibodies according to certain embodiments of the present invention comprise the humanized sequences provided in SEQ ID NOs:9, 10, 19 and 20.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato, K., et al., (1993) *Cancer Res* 53:851-856. Riechmann, L., et al., (1988) *Nature* 332:323-327; Verhoeyen, M., et al., (1988) *Science* 239:1534-1536; Kettleborough, C. A., et al., (1991) *Protein Engineering* 4:773-3783; Maeda, H., et al., (1991) *Human Antibodies Hybridoma* 2:124-134; Gorman, S. D., et al., (1991) *Proc Natl Acad Sci USA* 88:4181-4185; Tempest, P. R., et al., (1991) *Bio/Technology* 9:266-271; Co, M. S., et al., (1991) *Proc Natl Acad Sci USA* 88:2869-2873; Carter, P., et al., (1992) *Proc Natl Acad Sci USA* 89:4285-4289; and Co, M. S. et al., (1992) *J Immunol* 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies of the present disclosure may be chimeric antibodies. In this regard, a chimeric antibody is comprised of an antigen-binding fragment of an anti-IL-6R antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the anti-IL-6R antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

In certain embodiments, an IL-6R-binding antibody comprises one or more of the CDRs of the antibodies described herein. In this regard, it has been shown in some cases that the transfer of only the VHCDR3 of an antibody can be performed while still retaining desired specific binding (Barbas et al., *PNAS* (1995) 92: 2529-2533). See also, McLane et al., *PNAS* (1995) 92:5214-5218, Barbas et al., *J. Am. Chem. Soc.* (1994) 116:2161-2162.

Marks et al (*Bio/Technology,* 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the presently described antibodies may be shuffled with repertoires of VH or VL domains lacking a CDR3, and the shuffled complete VH or VL domains combined with a cognate VL or VH domain to provide an antibody or antigen-binding fragment thereof that binds IL-6R. The repertoire may then be displayed in a suitable host system such as the phage display system of WO92/01047 so that suitable antibodies or antigen-binding fragments thereof may be selected. A repertoire may consist of at least from about $10^4$ individual members and upwards by several orders of magnitude, for example, to about from $10^6$ to $10^8$ or $10^{10}$ or more members. Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying one or more CDR-derived sequences of the herein described invention embodiments using random mutagenesis of one or more selected VH and/or VL genes to generate mutations within the entire variable domain. Such a technique is described by Gram et al (1992, Proc. Natl. Acad. Sci., USA, 89:3576-3580), who used error-prone PCR. Another method which may be used is to direct mutagenesis to CDR regions of VH or VL genes. Such techniques are disclosed by Barbas et al., (1994, Proc. Natl. Acad. Sci., USA, 91:3809-3813) and Schier et al (1996, J. Mol. Biol. 263:551-567).

In certain embodiments, a specific VH and/or VL of the antibodies described herein may be used to screen a library of the complementary variable domain to identify antibodies with desirable properties, such as increased affinity for IL-6R. Such methods are described, for example, in Portolano et al., J. Immunol. (1993) 150:880-887; Clarkson et al., Nature (1991) 352:624-628.

Other methods may also be used to mix and match CDRs to identify antibodies having desired binding activity, such as binding to IL-6R. For example: Klimka et al., *British Journal of Cancer* (2000) 83: 252-260, describe a screening process using a mouse VL and a human VH library with CDR3 and FR4 retained from the mouse VH. After obtaining antibodies, the VH was screened against a human VL library to obtain antibodies that bound antigen. Beiboer et al., J. Mol. Biol. (2000) 296:833-849 describe a screening process using an entire mouse heavy chain and a human light chain library. After obtaining antibodies, one VL was combined with a human VH library with the CDR3 of the mouse retained. Antibodies capable of binding antigen were obtained. Rader et al., PNAS (1998) 95:8910-8915 describe a process similar to Beiboer et al above.

These just-described techniques are, in and of themselves, known as such in the art. The skilled person will, however, be able to use such techniques to obtain antibodies or antigen-binding fragments thereof according to several embodiments of the invention described herein, using routine methodology in the art.

Also disclosed herein is a method for obtaining an antibody antigen binding domain specific for IL-6R antigen, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a specific binding member or an antibody antigen binding domain specific for IL-6R and optionally with one or more desired properties. The VL domains may have an amino acid sequence which is substantially as set out herein. An analogous method may be employed in which one or more sequence variants of a VL domain disclosed herein are combined with one or more VH domains.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an IL-6R epitope is an antibody that binds one IL-6R epitope with greater affinity, avidity, more readily, and/or with greater duration than it binds to other IL-6R epitopes or non-IL-6R epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) *Annual Rev. Biochem.* 59:439-473.

In certain embodiments, the anti-IL-6R antibodies described herein have an affinity of about 100, 150, 155, 160, 170, 175, 180, 185, 190, 191, 192, 193, 194, 195, 196, 197, 198 or 199 picomolar, and in some embodiments, the antibodies may have even higher affinity for IL-6R.

The term "immunologically active", with reference to an epitope being or "remaining immunologically active", refers to the ability of an antibody (e.g., anti-IL-6R antibody) to bind to the epitope under different conditions, for example, after the epitope has been subjected to reducing and denaturing conditions.

An antibody or antigen-binding fragment thereof according to certain preferred embodiments of the present application may be one that competes for binding to IL-6R with any antibody described herein which both (i) specifically binds to the antigen and (ii) comprises a VH and/or VL domain disclosed herein, or comprises a VH CDR3 disclosed herein, or a variant of any of these. Competition between antibodies may be assayed easily in vitro, for example using ELISA and/or by tagging a specific reporter molecule to one antibody which can be detected in the presence of other untagged antibodies, to enable identification of specific antibodies which bind the same epitope or an overlapping epitope. Such assays are described, for example, in Example 1 where it was determined that the anti-IL-6R antibody of clone #51 disclosed herein binds to an epitope unique from the known anti-IL-6R antibody, tocilizumab. Thus, there is provided herein a specific antibody or antigen-binding fragment thereof, comprising a human antibody antigen-binding site which competes with an antibody described herein that binds to IL-6R.

In this regard, as used herein, the terms "competes with", "inhibits binding" and "blocks binding" (e.g., referring to inhibition/blocking of binding of IL-6 to IL-6R or referring to inhibition/blocking of binding of an anti-IL-6R antibody to IL-6R) are used interchangeably and encompass both partial and complete inhibition/blocking. The inhibition/blocking of IL-6 to IL-6R preferably reduces or alters the normal level or type of cell signaling that occurs when IL-6 binds to IL-6R without inhibition or blocking. Inhibition and blocking are also intended to include any measurable decrease in the binding of IL-6 to IL-6R when in contact with an anti-IL-6R antibody as disclosed herein as compared to the ligand not in contact with an anti-IL-6R antibody, e.g., the blocking of IL-6 to IL-6R by at least about 10%, 20%, 30%, 40%, 50%, 60%, 65%, 70%, 75%, 80%, 85%, 90%, 91%, 92%, 93%, 94%, 95%, 96%, 97%, 98%, 99%, or 100%.

The constant regions of immunoglobulins show less sequence diversity than the variable regions, and are responsible for binding a number of natural proteins to elicit important biochemical events. In humans there are five different classes of antibodies including IgA (which includes subclasses IgA1 and IgA2), IgD, IgE, IgG (which includes subclasses IgG1, IgG2, IgG3, and IgG4), and IgM. The distinguishing features between these antibody classes are their constant regions, although subtler differences may exist in the V region.

The Fc region of an antibody interacts with a number of Fc receptors and ligands, imparting an array of important functional capabilities referred to as effector functions. For IgG the Fc region comprises Ig domains CH2 and CH3 and the N-terminal hinge leading into CH2. An important family of Fc receptors for the IgG class are the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack.

The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). All FcγRs bind the same region on Fc, at the N-terminal end of the Cg2 (CH2) domain and the preceding hinge. This interaction is well characterized structurally (Sondermann et al., 2001, J Mol Biol 309:737-749), and several structures of the human Fc bound to the extracellular domain of human FcγRIIIb have been solved (pdb accession code 1E4K) (Sondermann et al., 2000, Nature 406:267-273.) (pdb accession codes 1IIS and 1IIX) (Radaev et al., 2001, J Biol Chem 276:16469-16477.)

The different IgG subclasses have different affinities for the FcγRs, with IgG1 and IgG3 typically binding substantially better to the receptors than IgG2 and IgG4 (Jefferis et al., 2002, Immunol Lett 82:57-65). All FcγRs bind the same region on IgG Fc, yet with different affinities: the high affinity binder FcγRI has a Kd for IgG1 of $10^{-8}$ $M^{-1}$, whereas the low affinity receptors FcγRII and FcγRIII generally bind at $10^{-6}$ and $10^{-5}$ respectively. The extracellular domains of FcγRIIIa and FcγRIIIb are 96% identical, however FcγRIIIb does not have a intracellular signaling domain. Furthermore, whereas FcγRI, FcγRIIa/c, and FcγRIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. The receptors also differ in expression pattern and levels on different immune cells. Yet another level of complexity is the existence of a number of FcγR polymorphisms in the human proteome. A particularly relevant polymorphism with clinical significance is V158/F158 FcγRIIIa. Human IgG1 binds with greater affinity to the V158 allotype than to the F158 allotype. This difference in affinity, and presumably its effect on ADCC and/or ADCP, has been shown to be a significant determinant of the efficacy of the anti-CD20 antibody rituximab (Rituxan®, a registered trademark of IDEC Pharmaceuticals Corporation). Patients with the V158 allotype respond favorably to rituximab treatment; however, patients with the lower affinity F158 allotype respond poorly (Cartron et al., 2002, Blood 99:754-758). Approximately 10-20% of humans are V158N158 homozygous, 45% are V158/F158 heterozygous, and 35-45% of humans are F158/F158 homozygous (Lehrnbecher et al., 1999, Blood 94:4220-4232; Cartron et al., 2002, Blood 99:754-758). Thus 80-90% of humans are poor responders, that is they have at least one allele of the F158 FcγRIIIa.

The Fc region is also involved in activation of the complement cascade. In the classical complement pathway, C1 binds with its C1q subunits to Fc fragments of IgG or IgM, which has formed a complex with antigen(s). In certain embodiments of the invention, modifications to the Fc region comprise modifications that alter (either enhance or decrease) the ability of an IL-6R-specific antibody as described herein to activate the complement system (see e.g., U.S. Pat. No. 7,740,847). To assess complement activation, a complement-dependent cytotoxicity (CDC) assay may be performed (See, e.g., Gazzano-Santoro et al., J. Immunol. Methods, 202:163 (1996)).

Thus in certain embodiments, the present invention provides anti-IL-6R antibodies having a modified Fc region with altered functional properties, such as reduced CDC, enhanced CDC, ADCC, or ADCP activity or enhanced binding affinity for a specific FcγR or increased serum half-life. Other modified Fc regions contemplated herein are described, for example, in issued U.S. Pat. Nos. 7,317,091; 7,657,380; 7,662,925; 6,538,124; 6,528,624; 7,297,775; 7,364,731; Published U.S. Applications US2009092599; US20080131435; US20080138344; and published International Applications WO2006/105338; WO2004/063351; WO2006/088494; WO2007/024249.

Thus, in certain embodiments, antibody variable domains with the desired binding specificities are fused to immunoglobulin constant domain sequences. In certain embodiments, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Antibodies of the present invention (and antigen-binding fragments and variants thereof) may also be modified to include an epitope tag or label, e.g., for use in purification or diagnostic applications. There are many linking groups known in the art for making antibody conjugates, including, for example, those disclosed in U.S. Pat. No. 5,208,020 or EP Patent 0 425 235 B1, and Chari et al., Cancer Research 52: 127-131 (1992). The linking groups include disufide groups, thioether groups, acid labile groups, photolabile groups, peptidase labile groups, or esterase labile groups, as disclosed in the above-identified patents, disulfide and thioether groups being preferred.

In another contemplated embodiment, an anti-IL-6R-specific antibody as described herein may be conjugated or operably linked to another therapeutic compound, referred to herein as a conjugate. The conjugate may be a cytotoxic agent, a chemotherapeutic agent, a cytokine, an anti-angiogenic agent, a tyrosine kinase inhibitor, a toxin, a radioisotope, or other therapeutically active agent. Chemotherapeutic agents, cytokines, anti-angiogenic agents, tyrosine kinase inhibitors, and other therapeutic agents have been described above, and all of these aforementioned therapeutic agents may find use as antibody conjugates.

In an alternate embodiment, the antibody is conjugated or operably linked to a toxin, including but not limited to small molecule toxins and enzymatically active toxins of bacterial, fungal, plant or animal origin, including fragments and/or variants thereof. Small molecule toxins include but are not limited to saporin (Kuroda K, et al., The Prostate 70:1286-1294 (2010); Lip, W L. et al., 2007 Molecular Pharmaceutics 4:241-251; Quadros E V., et al., 2010 Mol Cancer Ther; 9(11); 3033-40; Polito L., et al. 2009 British Journal of Haematology, 147, 710-718), calicheamicin, maytansine (U.S. Pat. No. 5,208,020), trichothene, and CC1065. Toxins include but are not limited to RNase, gelonin, enediynes, ricin, abrin, diptheria toxin, cholera toxin, gelonin, *Pseudomonas* exotoxin (PE40), *Shigella* toxin, *Clostridium perfringens* toxin, and pokeweed antiviral protein.

In one embodiment, an antibody or antigen-binding fragment thereof of the disclosure is conjugated to one or more maytansinoid molecules. Maytansinoids are mitototic inhibitors that act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533. Immunoconjugates containing maytansinoids and their therapeutic use are disclosed, for example, in U.S. Pat. Nos. 5,208,020, 5,416,064 and European Patent EP 0 425 235 B1. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

Another conjugate of interest comprises an antibody conjugated to one or more calicheamicin molecules. The calicheamicin family of antibiotics are capable of producing double-stranded DNA breaks at sub-picomolar concentrations. Structural analogues of calicheamicin that may also be used (Hinman et al., 1993, Cancer Research 53:3336-3342; Lode et al., 1998, Cancer Research 58:2925-2928) (U.S. Pat. No. 5,714,586; U.S. Pat. No. 5,712,374; U.S. Pat. No. 5,264,586; U.S. Pat. No. 5,773,001). Dolastatin 10 analogs such as auristatin E (AE) and monomethylauristatin E (MMAE) may find use as conjugates for the presently disclosed antibodies, or variants thereof (Doronina et al., 2003, Nat Biotechnol 21(7):778-84; Francisco et al., 2003 Blood 102(4):1458-65). Useful enzymatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, PCT WO 93/21232. The present disclosure further contemplates embodiments in which a conjugate or fusion is formed between an IL-6R-specific antibody as described herein and a compound with nucleolytic activity, for example a ribonuclease or DNA endonuclease such as a deoxyribonuclease (DNase).

In an alternate embodiment, a herein-disclosed antibody may be conjugated or operably linked to a radioisotope to form a radioconjugate. A variety of radioactive isotopes are available for the production of radioconjugate antibodies. Examples include, but are not limited to $^{90}Y$, $^{123}I$, $^{125}I$, $^{131}I$, $^{186}Re$, $^{188}Re$, $^{211}At$, and $^{212}Bi$.

Antibodies described herein may in certain other embodiments be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxel/paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, saporin, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine).

Moreover, an IL-6R-specific antibody (including a functional fragment thereof as provided herein such as an antigen-binding fragment) may in certain embodiments be conjugated to therapeutic moieties such as a radioactive materials or macrocyclic chelators useful for conjugating radiometal ions. In certain embodiments, the macrocyclic chelator is 1,4,7,10-tetraazacyclododecane-N,N',N",N"'-tetraacetic acid (DOTA) which can be attached to the antibody via a linker molecule. Such linker molecules are commonly known in the art and described in Denardo et al., 1998, Clin Cancer Res. 4:2483-90; Peterson et al., 1999, Bioconjug. Chem. 10:553; and Zimmerman et al., 1999, Nucl. Med. Biol. 26:943-50.

In yet another embodiment, an antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the antibody is conjugated or operably linked to an enzyme in order to employ Antibody Dependent Enzyme Mediated Prodrug Therapy (ADEPT). ADEPT may be used by conjugating or operably linking the antibody to a prodrug-activating enzyme that converts a prodrug (e.g. a peptidyl chemotherapeutic agent, see PCT WO 81/01145) to an active anti-cancer drug. See, for example, PCT WO 88/07378 and U.S. Pat. No. 4,975,278. The enzyme component of the immunoconjugate useful for ADEPT includes any enzyme capable of acting on a prodrug in such a way so as to convert it into its more active, cytotoxic form. Enzymes that are useful in the method of these and related embodiments include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuramimidase useful for converting glycosylated prodrugs into free drugs; beta-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", may be used to convert prodrugs into free active drugs (see, for example, Massey, 1987, Nature 328: 457-458). Antibody-abzyme conjugates can be prepared for delivery of the abzyme to a tumor cell population.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particular coupling agents include N-succinimidyl-3-(2-pyridyldithio) propionate (SPDP) (Carlsson et al., Biochem. J. 173:723-737 [1978]) and N-succinimidyl-4-(2-pyridylthio)pentanoate (SPP) to provide for a disulfide linkage. The linker may be a "cleavable linker" facilitating release of one or more cleavable components. For example, an acid-labile linker may be used (Cancer Research 52: 127-131 (1992); U.S. Pat. No. 5,208,020).

Other modifications of the antibodies (and polypeptides) of the invention are also contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980).

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

The desired functional properties of anti-IL-6R antibodies may be assessed using a variety of methods known to the skilled person affinity/binding assays (for example, surface plasmon resonance, competitive inhibition assays); cytotoxicity assays, cell viability assays, cell proliferation or differentiation assays in response to IL-6 (e.g., TF-1 cell proliferation assays), cancer cell and/or tumor growth inhibition using in vitro or in vivo models. Other assays may test the ability of antibodies described herein to block normal IL-6/IL-6R-mediated responses, such as STAT3 phosphorylation or STAT3 signaling events, or other downstream signaling events. The antibodies described herein may also be tested for effects on IL-6R receptor internalization, in vitro and in vivo efficacy, etc. Such assays may be performed using well-established protocols known to the skilled person (see e.g., Current Protocols in Molecular Biology (Greene Publ. Assoc. Inc. & John Wiley & Sons, Inc., NY, N.Y.); Current Protocols in Immunology (Edited by: John E. Coligan, Ada M. Kruisbeek, David H. Margulies, Ethan M. Shevach, Warren Strober 2001 John Wiley & Sons, NY, N.Y.); or commercially available kits.

The present invention further provides in certain embodiments an isolated nucleic acid encoding an antibody or antigen-binding fragment thereof as described herein, for instance, a nucleic acid which codes for a CDR or VH or VL domain as described herein. Nucleic acids include DNA and RNA. These and related embodiments may include polynucleotides encoding antibodies that bind IL-6R as described herein. The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, Nucl. Acids Res., 14:9081; Stec et al., 1984, J. Am. Chem. Soc., 106:6077; Stein et al., 1988, Nucl. Acids Res., 16:3209; Zon et al., 1991, Anti-Cancer Drug Design, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, Chemical Reviews, 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell. The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

As will be understood by those skilled in the art, polynucleotides may include genomic sequences, extra-genomic and plasmid-encoded sequences and smaller engineered gene segments that express, or may be adapted to express, proteins, polypeptides, peptides and the like. Such segments may be naturally isolated, or modified synthetically by the skilled person.

As will be also recognized by the skilled artisan, polynucleotides may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide according to the present disclosure, and a polynucleotide may, but need not, be linked to other molecules and/or support materials. Polynucleotides may comprise a native sequence or may comprise a sequence that encodes a variant or derivative of such a sequence.

Therefore, according to these and related embodiments, the present disclosure also provides polynucleotides encoding the anti-IL-6R antibodies described herein. In certain embodiments, polynucleotides are provided that comprise some or all of a polynucleotide sequence encoding an antibody as described herein and complements of such polynucleotides.

In other related embodiments, polynucleotide variants may have substantial identity to a polynucleotide sequence encoding an anti-IL-6R antibody described herein. For example, a polynucleotide may be a polynucleotide comprising at least 70% sequence identity, preferably at least 75%, 80%, 85%, 90%, 95%, 96%, 97%, 98%, or 99% or higher, sequence identity compared to a reference polynucleotide sequence such as a sequence encoding an antibody described herein, using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the binding affinity of the antibody encoded by the variant polynucleotide is not substantially diminished relative to an antibody encoded by a polynucleotide sequence specifically set forth herein.

In certain other related embodiments, polynucleotide fragments may comprise or consist essentially of various lengths of contiguous stretches of sequence identical to or complementary to a sequence encoding an antibody as described herein. For example, polynucleotides are provided that comprise or consist essentially of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 120, 130, 140, 150, 200, 300, 400, 500 or 1000 or more contiguous nucleotides of a sequences the encodes an antibody, or antigen-binding fragment thereof, disclosed herein as well as all intermediate lengths there between. It will be readily understood that "intermediate lengths", in this context, means any length between the quoted values, such as 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of a polynucleotide encoding an antibody described herein or at both ends of a polynucleotide encoding an antibody described herein.

In another embodiment, polynucleotides are provided that are capable of hybridizing under moderate to high stringency conditions to a polynucleotide sequence encoding an antibody, or antigen-binding fragment thereof, provided herein, or a fragment thereof, or a complementary sequence thereof. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.-65° C. or 65° C.-70° C.

In certain embodiments, the polynucleotides described above, e.g., polynucleotide variants, fragments and hybridizing sequences, encode antibodies that bind IL-6R, or antigen-binding fragments thereof. In other embodiments, such polynucleotides encode antibodies or antigen-binding fragments, or CDRs thereof, that bind to IL-6R at least about 50%, at least about 70%, and in certain embodiments, at least about 90% as well as an antibody sequence specifically set forth herein. In further embodiments, such polynucleotides encode antibodies or antigen-binding fragments, or CDRs thereof, that bind to IL-6R with greater affinity than the antibodies set forth herein, for example, that bind quantitatively at least about 105%, 106%, 107%, 108%, 109%, or 110% as well as an antibody sequence specifically set forth herein.

As described elsewhere herein, determination of the three-dimensional structures of representative polypeptides (e.g., variant IL-6R-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. A variety of computer programs are known to the skilled artisan for determining appropriate amino acid substitutions (or appropriate polynucleotides encoding the amino acid sequence) within an antibody such that, for example, affinity is maintained or better affinity is achieved.

The polynucleotides described herein, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., *Unified Approach to Alignment and Phylogenes*, pp. 626-645 (1990); *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Santou, N. Nes, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode an antibody as described herein. Some of these polynucleotides bear minimal sequence identity to the nucleotide sequence of the native or original polynucleotide sequence that encode antibodies that bind to IL-6R. Nonetheless, polynucleotides that vary due to differences in codon usage are expressly contemplated by the present disclosure. In certain embodiments, sequences that have been codon-optimized for mammalian expression are specifically contemplated.

Therefore, in another embodiment of the invention, a mutagenesis approach, such as site-specific mutagenesis, may be employed for the preparation of variants and/or derivatives of the antibodies described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the inventors contemplate the mutagenesis of the polynucleotide sequences that encode an antibody disclosed herein, or an antigen-binding fragment thereof, to alter one or more properties of the encoded polypeptide, such as the binding affinity of the antibody or the antigen-binding fragment thereof, or the function of a particular Fc region, or the affinity of the Fc region for a particular FcγR. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification.

As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants, recursive sequence recombination, as described in U.S. Pat. No. 5,837,458, may be employed. In this approach, iterative cycles of recombination and screening or selection are performed to "evolve" individual polynucleotide variants having, for example, increased binding affinity. Certain embodiments also provide constructs in the form of plasmids, vectors, transcription or expression cassettes which comprise at least one polynucleotide as described herein.

According to certain related embodiments there is provided a recombinant host cell which comprises one or more constructs as described herein; a nucleic acid encoding any antibody, CDR, VH or VL domain, or antigen-binding fragment thereof; and a method of production of the encoded product, which method comprises expression from encoding nucleic acid therefor. Expression may conveniently be achieved by culturing under appropriate conditions recombinant host cells containing the nucleic acid. Following production by expression, an antibody or antigen-binding fragment thereof, may be isolated and/or purified using any suitable technique, and then used as desired.

Antibodies or antigen-binding fragments thereof as provided herein, and encoding nucleic acid molecules and vectors, may be isolated and/or purified, e.g. from their natural environment, in substantially pure or homogeneous form, or, in the case of nucleic acid, free or substantially free of nucleic acid or genes of origin other than the sequence encoding a polypeptide with the desired function. Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli.*

The expression of antibodies and antigen-binding fragments in prokaryotic cells such as *E. coli* is well established in the art. For a review, see for example Pluckthun, A. Bio/Technology 9: 545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the herein described antibodies, and which further expresses or is capable of expressing a selected gene of interest, such as a gene encoding any herein described antibody. The term includes the progeny of the parent cell, whether or not the progeny are identical in morphology or in genetic make-up to the original parent, so long as the selected gene is present. Accordingly there is also contemplated a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. In one embodiment, the nucleic acid is integrated into the genome (e.g. chromosome) of the host cell. Integration may be promoted by inclusion of sequences which promote recombination with the genome, in accordance-with standard techniques.

The present invention also provides, in certain embodiments, a method which comprises using a construct as stated above in an expression system in order to express a particular polypeptide such as an IL-6R-specific antibody as described herein. The term "transduction" is used to refer to the transfer of genes from one bacterium to another, usually by a phage. "Transduction" also refers to the acquisition and transfer of eukaryotic cellular sequences by retroviruses. The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, Gene 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "naturally occurring" or "native" when used in connection with biological materials such as nucleic acid molecules, polypeptides, host cells, and the like, refers to materials which are found in nature and are not manipulated by a human. Similarly, "non-naturally occurring" or "non-native" as used herein refers to a material that is not found in nature or that has been structurally modified or synthesized by a human.

The terms "polypeptide" "protein" and "peptide" and "glycoprotein" are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the antibodies that bind to IL-6R of the present disclosure, or sequences that have deletions from, additions to, and/or substitutions of one or more amino acid of an anti-IL-6R antibody. Thus, a "polypeptide" or a "protein" can comprise one (termed "a monomer") or a plurality (termed "a multimer") of amino acid chains.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

The term "polypeptide fragment" refers to a polypeptide, which can be monomeric or multimeric, that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies. In the case of an anti-IL-6R antibody, useful fragments include, but are not limited to: a CDR region, especially a CDR3 region of the heavy or light chain; a variable region of a heavy or light chain; a portion of an antibody chain or just its variable region including two CDRs; and the like.

Polypeptides may comprise a signal (or leader) sequence at the N-terminal end of the protein, which co-translationally or post-translationally directs transfer of the protein. The polypeptide may also be fused in-frame or conjugated to a linker or other sequence for ease of synthesis, purification or identification of the polypeptide (e.g., poly-His), or to enhance binding of the polypeptide to a solid support.

A peptide linker/spacer sequence may also be employed to separate multiple polypeptide components by a distance sufficient to ensure that each polypeptide folds into its secondary and/or tertiary structures, if desired. Such a peptide linker sequence can be incorporated into a fusion polypeptide using standard techniques well known in the art.

Certain peptide spacer sequences may be chosen, for example, based on: (1) their ability to adopt a flexible extended conformation; (2) their inability to adopt a secondary structure that could interact with functional epitopes on the first and second polypeptides; and/or (3) the lack of hydrophobic or charged residues that might react with the polypeptide functional epitopes.

In one illustrative embodiment, peptide spacer sequences contain, for example, Gly, Asn and Ser residues. Other near neutral amino acids, such as Thr and Ala, may also be included in the spacer sequence.

Other amino acid sequences which may be usefully employed as spacers include those disclosed in Maratea et al., Gene 40:39 46 (1985); Murphy et al., Proc. Natl. Acad. Sci. USA 83:8258 8262 (1986); U.S. Pat. No. 4,935,233 and U.S. Pat. No. 4,751,180.

Other illustrative spacers may include, for example, Glu-Gly-Lys-Ser-Ser-Gly-Ser-Gly-Ser-Glu-Ser-Lys-Val-Asp (Chaudhary et al., 1990, Proc. Natl. Acad. Sci. U.S.A. 87:1066-1070; SEQ ID NO:105) and Lys-Glu-Ser-Gly-Ser-Val-Ser-Ser-Glu-Gln-Leu-Ala-Gln-Phe-Arg-Ser-Leu-Asp (Bird et al., 1988, Science 242:423-426; SEQ ID NO:106).

In some embodiments, spacer sequences are not required when the first and second polypeptides have non-essential N-terminal amino acid regions that can be used to separate the functional domains and prevent steric interference. Two coding sequences can be fused directly without any spacer or by using a flexible polylinker composed, for example, of the pentamer Gly-Gly-Gly-Gly-Ser (SEQ ID NO:107) repeated 1 to 3 times. Such a spacer has been used in constructing single chain antibodies (scFv) by being inserted between VH and VL (Bird et al., 1988, Science 242:423-426; Huston et al., 1988, Proc. Natl. Acad. Sci. U.S.A. 85:5979-5883).

A peptide spacer, in certain embodiments, is designed to enable the correct interaction between two beta-sheets forming the variable region of the single chain antibody.

In certain illustrative embodiments, a peptide spacer is between 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids.

In other illustrative embodiments, a peptide spacer comprises about 1, 5, 10, 15, 20, 25, 30, 35, 40, 45, 50 or more amino acids in length.

Amino acid sequence modification(s) of the antibodies described herein are contemplated. For example, it may be desirable to improve the binding affinity and/or other biological properties of the antibody. For example, amino acid sequence variants of an antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics (e.g., high affinity binding to IL-6R). The amino acid changes also may alter post-translational processes of the antibody, such as changing the number or position of glycosylation sites. Any of the variations and modifications described above for polypeptides of the present invention may be included in antibodies of the present invention.

The present disclosure provides variants of the antibodies disclosed herein. In certain embodiments, such variant antibodies or antigen-binding fragments, or CDRs thereof, bind to IL-6R at least about 50%, at least about 70%, and in certain embodiments, at least about 90% as well as an antibody sequence specifically set forth herein. In further embodiments, such variant antibodies or antigen-binding fragments, or CDRs thereof, bind to IL-6R with greater affinity than the antibodies set forth herein, for example, that bind quantitatively at least about 105%, 106%, 107%, 108%, 109%, or 110% as well as an antibody sequence specifically set forth herein.

In particular embodiments, a subject antibody may have: a) a heavy chain variable domain having an amino acid sequence that is at least 80% identical, at least 95% identical, at least 90%, at least 95% or at least 98% or 99% identical, to the heavy chain variable region of an anti-IL-6R antibody described herein; and b) a light chain variable region having an amino acid sequence that is at least 80% identical, at least 85%, at least 90%, at least 95% or at least 98% or 99% identical, to the light chain variable domain of an anti-IL-6R antibody described herein. The amino acid sequence of illustrative heavy and light chain regions are set forth in SEQ ID NOs:1, 2, 9-12, 19, 20 and 25-44).

In particular embodiments, the antibody may comprise: a) a heavy chain variable region comprising: i. a CDR1 region that is identical in amino acid sequence to the heavy chain CDR1 region of a selected antibody described herein; ii. a CDR2 region that is identical in amino acid sequence to the heavy chain CDR2 region of a selected antibody described herein; and iii. a CDR3 region that is identical in amino acid sequence to the heavy chain CDR3 region of a selected antibody as described herein; and b) a light chain variable domain comprising: i. a CDR1 region that is identical in amino acid sequence to the light chain CDR1 region of a selected antibody described herein; ii. a CDR2 region that is identical in amino acid sequence to the light chain CDR2 region of a selected antibody described herein; and iii. a CDR3 region that is identical in amino acid sequence to the light chain CDR3 region of a selected antibody described herein; wherein the antibody specifically binds a selected target (e.g., IL-6R). In a further embodiment, the antibody, or antigen-binding fragment thereof, is a variant antibody wherein the variant comprises a heavy and light chain identical to the selected antibody except for up to 8, 9, 10, 11, 12, 13, 14, 15, or more amino acid substitutions in the CDR regions of the VH and VL regions. In this regard, there may be 1, 2, 3, 4, 5, 6, 7, 8, or in certain embodiments, 9, 10, 11, 12, 13, 14, 15 more amino acid substitutions in the CDR regions of a selected antibody. Substitutions may be in CDRs either in the VH and/or the VL regions. (See e.g., Muller, 1998, Structure 6:1153-1167).

Determination of the three-dimensional structures of representative polypeptides (e.g., variant IL-6R-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. See, for instance, Donate et al., 1994 Prot. Sci. 3:2378; Bradley et al., Science 309: 1868-1871 (2005); Schueler-Furman et al., Science 310:638 (2005); Dietz et al., Proc. Nat. Acad. Sci. USA 103:1244 (2006); Dodson et al., Nature 450:176 (2007); Qian et al., Nature 450:259 (2007); Raman et al. Science 327:1014-1018 (2010). Some additional non-limiting examples of computer algorithms that may be used for these and related embodiments, such as for rational design of IL-6R-specific antibodies antigen-binding domains thereof as provided herein, include VMD which is a molecular visualization program for displaying, animating, and analyzing large biomolecular systems using 3-D graphics and built-in scripting (see the website for the Theoretical and Computational Biophysics Group, University of Illinois at Urbana-Champagne, at ks.uiuc.edu/Research/vmd/. Many other computer programs are known in the art and available to the skilled person and which allow for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) J. Comput. Chem. 4:187-217) and AMBER (Weiner et al (1981) J. Comput. Chem. 106: 765), which assess force field calculations, and analysis (see also, Eisenfield et al. (1991) Am. J. Physiol. 261:C376-386; Lybrand (1991) J. Pharm. Belg. 46:49-54; Froimowitz (1990) Biotechniques 8:640-644; Burbam et al. (1990) Proteins 7:99-111; Pedersen (1985) Environ. Health Perspect. 61:185-190; and Kini et al. (1991) J. Biomol. Struct. Dyn. 9:475-488). A variety of appropriate computational computer programs are also commercially available, such as from Schrödinger (Munich, Germany).

In another embodiment of invention, the anti-IL-6R antibodies and humanized versions thereof are derived from rabbit monoclonal antibodies, and in particular are generated using RABMAB® rabbit monoclonal antibody technology. These antibodies are advantageous as they require minimal sequence modifications, thereby facilitating retention of functional properties after humanization using mutational lineage guided (MLG) humanization technology (see e.g., U.S. Pat. No. 7,462,697). Thus, illustrative methods for making the anti-IL-6R antibodies of the present disclosure include the RABMAB® rabbit monoclonal antibody technology described, for example, in U.S. Pat. Nos. 5,675,063 and 7,429,487. In this regard, in certain embodiments, the anti-IL-6R antibodies of the disclosure are produced in rabbits. In particular embodiments, a rabbit-derived immortal B-lymphocyte capable of fusion with a rabbit splenocyte is used to produce a hybrid cell that produces an antibody. The immortal B-lymphocyte does not detectably express endogenous immunoglobulin heavy chain and may contain, in certain embodiments, an altered immunoglobulin heavy chain-encoding gene.

Compositions and Methods of Use

The present disclosure provides compositions comprising the IL-6R-specific antibodies, antigen-binding fragments thereof and administration of such composition in a variety of therapeutic settings.

The term "subject" is intended to include any mammal or indeed any vertebrate that may be used as a model system for human disease. Examples of subjects include humans, monkeys, apes, dogs, cats, mice, rats, fish, zebra fish, birds, horses, pigs, cows, sheep, goats, chickens, ducks, donkeys, turkeys, peacocks, chinchillas, ferrets, gerbils, rabbits, guinea pigs, hamsters and transgenic species thereof. In particular embodiments, a subject is a human patient having a particular disease in need of treatment, as described further herein.

Administration of the IL-6R-specific antibodies described herein, in pure form or in an appropriate pharmaceutical composition, can be carried out via any of the accepted modes of administration of agents for serving similar utilities. The pharmaceutical compositions can be prepared by combining an antibody or antibody-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical. Preferred modes of administration depend upon the nature of the condition to be treated or prevented. An amount that, following administration, reduces, inhibits, prevents or delays the progression and/or metastasis of a cancer is considered effective.

In certain embodiments, the amount administered is sufficient to result in tumor regression, as indicated by a statistically significant decrease in the amount of viable tumor, for example, at least a 50% decrease in tumor mass, or by altered (e.g., decreased with statistical significance) scan dimensions. In other embodiments, the amount administered is sufficient to result in clinically relevant reduction in rheumatoid arthritis symptoms, such as, but not limited to, reduction of any one or more of fatigue, loss of appetite, low fever, swollen glands, weakness, swollen joints, joint pain, morning stiffness, warm, tender, and stiff joints when not used for as little as an hour, bilateral joint pain (fingers (but not the fingertips), wrists, elbows, shoulders, hips, knees, ankles, toes, jaw, and neck may be affected); loss of range of motion of affected joints, pleurisy, eye burning, eye itching, eye discharge, nodules under the skin, numbness, tingling, or burning in the hands and feet.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The IL-6R-specific antibody-containing compositions may be administered alone or in combination with other known cancer treatments, such as radiation therapy, chemotherapy, transplantation, immunotherapy, hormone therapy, photodynamic therapy, etc. The compositions may also be administered in combination with antibiotics.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described IL-6R-specific antibody in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of an antibody of the present disclosure, for treatment of a disease or condition of interest in accordance with teachings herein.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of an IL-6R-specific antibody as herein disclosed such that a suitable dosage will be obtained. Typically, this amount is at least 0.01% of the antibody in the composition. When intended for oral administration, this amount may be varied to be between 0.1 and about 70% of the weight of the composition. Certain oral pharmaceutical compositions contain between about 4% and about 75% of the antibody. In certain embodiments, pharmaceutical compositions and preparations according to the present invention are prepared so that a parenteral dosage unit contains between 0.01 to 10% by weight of the antibody prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the antibody of the invention and thereby assists in the delivery of the compound. Suitable agents that may act in this capacity include other monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises an IL-6R-specific antibody as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the antibody composition so as to facilitate dissolution or homogeneous suspension of the antibody in the aqueous delivery system.

The compositions may be are administered in a therapeutically effective amount, which will vary depending upon a variety of factors including the activity of the specific compound (e.g., IL-6R-specific antibody) employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compositions comprising the IL-6R-specific antibodies of the present disclosure may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising antibodies of the invention and each active agent in its own separate pharmaceutical dosage formulation. For example, an antibody as described herein and the other active agent can be administered to the patient together in a single oral dosage composition such as a tablet or capsule, or each agent administered in separate oral dosage formulations. Similarly, an antibody as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising antibodies and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of anti-IL-6R antibody compositions of this disclosure in combination with one or more other therapeutic agents. Such therapeutic agents may be accepted in the art as a standard treatment for a particular disease state as described herein, such as rheumatoid arthritis, inflammation or cancer. Exemplary therapeutic agents contemplated include cytokines, growth factors, steroids, NSAIDs, DMARDs, anti-inflammatories, chemotherapeutics, radiotherapeutics, or other active and ancillary agents.

In certain embodiments, the anti-IL-6R antibodies disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the anti-IL-6R antibodies described herein. In one embodiment, the antibody is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

The compositions comprising herein described IL-6R-specific antibodies may be administered to a subject afflicted with a disease as described herein, such as an inflammatory disease or a cancer. In this regard, the compositions comprising IL-6R-specific antibodies as described herein may be administered to a subject having an inflammatory disease, such as but not limited to juvenile idiopathic arthritis, Crohn's disease, colitis, dermatitis, psoriasis, diverticulitis, hepatitis, irritable bowel syndrome (IBS), lupus erythematous, nephritis, Parkinson's disease, ulcerative colitis, multiple sclerosis (MS), Alzheimer's disease, arthritis, rheumatoid arthritis, asthma, and various cardiovascular diseases such as atherosclerosis and vasculitis. In certain embodiments, the inflammatory disease is selected from the group consisting of, diabetes, gout, cryopyrin-associated periodic syndrome, and chronic obstructive pulmonary disorder. In this regard, one embodiment provides a method of treating, reducing the severity of or preventing inflammation or an inflammatory disease by administering to a patient in need thereof a therapeutically effective amount of a herein disclosed compositions.

One embodiment provides a method of treating, reducing the severity of or preventing a cancer, including, but not limited to multiple myeloma, plasma cell leukemia, renal cell carcinoma, Kaposi's sarcoma, colorectal cancer, gastric cancer, melanoma, leukemia, lymphoma, glioma, glioblastoma multiforme, lung cancer (including but not limited to non-small cell lung cancer (NSCLC; both adenocarcinoma and squamous cell carcinoma)), non-Hodgkin's lymphoma, Hodgkin's disease, plasmocytoma, sarcoma, thymoma, breast cancer, prostate cancer, hepatocellular carcinoma, bladder cancer, uterine cancer, pancreatic cancer, esophageal cancer, brain cancer, head and neck cancers, ovarian cancer, cervical cancer, testicular cancer, stomach cancer, esophageal cancer, hepatoma, acute lymphoblastic leukemia (ALL), T-ALL, acute myelogenous leukemia (AML), chronic myelogenous leukemia (CML), and chronic lymphocytic leukemia (CLL), salivary carcinomas, or other cancers.

Another embodiment of the present disclosure provides a method of treating, reducing the severity of or preventing a disease selected from the group consisting of sepsis, bone resorption (osteoporosis), cachexia, cancer-related fatigue, psoriasis, systemic-onset juvenile idiopathic arthritis, systemic lupus erythematosus (SLE), mesangial proliferative glomerulonephritis, hyper gammaglobulinemia, Castleman's disease, IgM gammopathy, cardiac myxoma and autoimmune insulin-dependent diabetes.

For in vivo use for the treatment of disease, in particular human disease, the antibodies described herein are generally incorporated into a pharmaceutical composition prior to administration. A pharmaceutical composition comprises one or more of the antibodies described herein in combination with a physiologically acceptable carrier or excipient as described elsewhere herein. To prepare a pharmaceutical composition, an effective amount of one or more of the compounds is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof.

The compositions comprising IL-6R-specific antibodies as described herein may be prepared with carriers that protect the antibody against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

Provided herein are methods of treatment using the antibodies that bind IL-6R. In one embodiment, an antibody of the present invention is administered to a patient having a disease involving inappropriate expression of IL-6, which is meant in the context of the present disclosure to include diseases and disorders characterized by aberrant IL-6 expression or activity, due for example to alterations (e.g., statistically significant increases or decreases) in the amount of a protein present, or the presence of a mutant protein, or both. An overabundance may be due to any cause, including but not limited to overexpression at the molecular level, prolonged or accumulated appearance at the site of action, or increased (e.g., in a statistically significant manner) activity of IL-6 (or IL-6R) relative to that which is normally detectable. Such an overabundance of IL-6 can be measured relative to normal expression, appearance, or activity of IL-6 or IL-6R signalling events, and said measurement may play an important role in the development and/or clinical testing of the antibodies described herein.

In particular, the present antibodies are useful for the treatment of a variety of cancers associated with the expression of IL-6. For example, one embodiment of the invention provides a method for the treatment of a cancer including, but not limited to, multiple myeloma, plasma cell leukemia, renal cell carcinoma, Kaposi's sarcoma, oral squamous cell carcinoma, pancreatic and colon carcinoma, by administering to a cancer patient a therapeutically effective amount of a herein disclosed IL-6R-specific antibody. An amount that, following administration, inhibits, prevents or delays the progression and/or metastasis of a cancer in a statistically significant manner (i.e., relative to an appropriate control as will be known to those skilled in the art) is considered effective.

Another embodiment provides a method for preventing metastasis of a cancer including, but not limited to, multiple myeloma, plasma cell leukemia, renal cell carcinoma, Kaposi's sarcoma, oral squamous cell carcinoma, pancreatic and colon carcinoma, by administering to a cancer patient a therapeutically effective amount of a herein disclosed IL-6R-specific antibody (e.g., an amount that, following administration, inhibits, prevents or delays metastasis of a cancer in a statistically significant manner, i.e., relative to an appropriate control as will be known to those skilled in the art).

Another embodiment provides a method for preventing a cancer including, but not limited to, multiple myeloma, plasma cell leukemia, renal cell carcinoma, Kaposi's sarcoma, oral squamous cell carcinoma, pancreatic and colon carcinoma, by administering to a cancer patient a therapeutically effective amount of a herein disclosed IL-6R-specific antibody.

Another embodiment provides a method for treating, inhibiting the progression of or prevention of sepsis, bone resorption (osteoporosis), cachexia, cancer-related fatigue, psoriasis, systemic-onset juvenile idiopathic arthritis, systemic lupus erythematosus (SLE), mesangial proliferative glomerulonephritis, rheumatoid arthritis, hyper gamma-globulinemia, Castleman's disease, IgM gammopathy, cardiac myxoma and autoimmune insulin-dependent diabetes by administering to a patient afflicted by one or more of these diseases a therapeutically effective amount of a herein disclosed IL-6R-specific antibody.

In another embodiment, anti-IL-6R antibodies of the present invention are used to determine the structure of bound antigen, e.g., conformational epitopes, which structure may then be used to develop compounds having or mimicking this structure, e.g., through chemical modeling and SAR methods.

Various other embodiments of the present invention relate, in part, to diagnostic applications for detecting the presence of cells or tissues expressing IL-6R. Thus, the present disclosure provides methods of detecting IL-6R in a sample, such as detection of cells or tissues expressing IL-6R. Such methods can be applied in a variety of known detection formats, including, but not limited to immunohistochemistry (IHC), immunocytochemistry (ICC), in situ hybridization (ISH), whole-mount in situ hybridization (WISH), fluorescent DNA in situ hybridization (FISH), flow cytometry, enzyme immuno-assay (EIA), and enzyme linked immuno-assay (ELISA).

ISH is a type of hybridization that uses a labeled complementary DNA or RNA strand (i.e., primary binding agent) to localize a specific DNA or RNA sequence in a portion or section of a cell or tissue (in situ), or if the tissue is small enough, the entire tissue (whole mount ISH). One having ordinary skill in the art would appreciate that this is distinct from immunohistochemistry, which localizes proteins in tissue sections using an antibody as a primary binding agent. DNA ISH can be used on genomic DNA to determine the structure of chromosomes. Fluorescent DNA ISH (FISH) can, for example, be used in medical diagnostics to assess chromosomal integrity. RNA ISH (hybridization histochemistry) is used to measure and localize mRNAs and other transcripts within tissue sections or whole mounts.

In various embodiments, the antibodies described herein are conjugated to a detectable label that may be detected directly or indirectly. In this regard, an antibody "conjugate" refers to an anti-IL-6R antibody that is covalently linked to a detectable label. In the present invention, DNA probes, RNA probes, monoclonal antibodies, antigen-binding fragments thereof, and antibody derivatives thereof, such as a single-chain-variable-fragment antibody or an epitope tagged antibody, may all be covalently linked to a detectable label. In "direct detection", only one detectable antibody is used, i.e., a primary detectable antibody. Thus, direct detection means that the antibody that is conjugated to a detectable label may be detected, per se, without the need for the addition of a second antibody (secondary antibody).

A "detectable label" is a molecule or material that can produce a detectable (such as visually, electronically or otherwise) signal that indicates the presence and/or concentration of the label in a sample. When conjugated to a antibody, the detectable label can be used to locate and/or quantify the target to which the specific antibody is directed. Thereby, the presence and/or concentration of the target in a sample can be detected by detecting the signal produced by the detectable label. A detectable label can be detected directly or indirectly, and several different detectable labels conjugated to different specific-antibodies can be used in combination to detect one or more targets.

Examples of detectable labels, which may be detected directly, include fluorescent dyes and radioactive substances and metal particles. In contrast, indirect detection requires the application of one or more additional antibodies, i.e., secondary antibodies, after application of the primary antibody. Thus, the detection is performed by the detection of the binding of the secondary antibody or binding agent to the primary detectable antibody. Examples of primary detectable binding agents or antibodies requiring addition of a secondary binding agent or antibody include enzymatic detectable binding agents and hapten detectable binding agents or antibodies.

In some embodiments, the detectable label is conjugated to a nucleic acid polymer which comprises the first binding agent (e.g., in an ISH, WISH, or FISH process). In other embodiments, the detectable label is conjugated to an antibody which comprises the first binding agent (e.g., in an IHC process).

Examples of detectable labels which may be conjugated to antibodies used in the methods of the present disclosure include fluorescent labels, enzyme labels, radioisotopes, chemiluminescent labels, electrochemiluminescent labels, bioluminescent labels, polymers, polymer particles, metal particles, haptens, and dyes.

Examples of fluorescent labels include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, green fluorescent protein (GFP) and analogues thereof, and conjugates of R-phycoerythrin or allophycoerythrin, inorganic fluorescent labels such as particles based on semiconductor material like coated CdSe nanocrystallites.

Examples of polymer particle labels include micro particles or latex particles of polystyrene, PMMA or silica, which can be embedded with fluorescent dyes, or polymer micelles or capsules which contain dyes, enzymes or substrates.

Examples of metal particle labels include gold particles and coated gold particles, which can be converted by silver stains. Examples of haptens include DNP, fluorescein isothiocyanate (FITC), biotin, and digoxigenin. Examples of enzymatic labels include horseradish peroxidase (HRP), alkaline phosphatase (ALP or AP), β-galactosidase (GAL), glucose-6-phosphate dehydrogenase, β-N-acetylglucosamimidase, β-glucuronidase, invertase, Xanthine Oxidase, firefly luciferase and glucose oxidase (GO). Examples of commonly used substrates for horseradishperoxidase include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), .alpha.-naphtol pyronin (.alpha.-NP), o-dianisidine (OD), 5-bromo-4-chloro-3-indolylphosphate (BCIP), Nitro blue tetrazolium (NBT), 2-(p-iodophenyl)-3-p-nitropheny-I-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B 1-phosphate/fast red TR (NABP/FR), Naphthol-AS-MX-phosphate/fast red TR (NAMP/FR), Naphthol-AS-B1-phosphate/-fast red TR (NABP/FR), Naphthol-AS-MX-phosphate/fast red TR (NAMP/FR), Naphthol-AS-B1-phosphate/new fuschin (NABP/NF), bromochloroindolyl phosphate/nitroblue tetrazolium (BCIP/NBT), 5-Bromo-4-chloro-3-indolyl-b-d-galactopyranoside (BCIG).

Examples of luminescent labels include luminol, isoluminol, acridinium esters, 1,2-dioxetanes and pyridopyridazines. Examples of electrochemiluminescent labels include ruthenium derivatives. Examples of radioactive labels include radioactive isotopes of iodide, cobalt, selenium, tritium, carbon, sulfur and phosphorous.

Detectable labels may be linked to the antibodies described herein or to any other molecule that specifically binds to a biological marker of interest, e.g., an antibody, a nucleic acid probe, or a polymer. Furthermore, one of ordinary skill in the art would appreciate that detectable labels can also be conjugated to second, and/or third, and/or fourth, and/or fifth binding agents or antibodies, etc. Moreover, the skilled artisan would appreciate that each additional binding agent or antibody used to characterize a biological marker of interest may serve as a signal amplification step. The biological marker may be detected visually using, e.g., light microscopy, fluorescent microscopy, electron microscopy where the detectable substance is for example a dye, a colloidal gold particle, a luminescent reagent. Visually detectable substances bound to a biological marker may also be detected using a spectrophotometer. Where the detectable substance is a radioactive isotope detection can be visually by autoradiography, or non-visually using a scintillation counter. See, e.g., Larsson, 1988, Immunocytochemistry: Theory and Practice, (CRC Press, Boca Raton, Fla.); Methods in Molecular Biology, vol. 80 1998, John D. Pound (ed.) (Humana Press, Totowa, N.J.).

The invention further provides kits for detecting IL-6R or cells or tissues expressing IL-6R in a sample, wherein the kits contain at least one antibody, polypeptide, polynucleotide, vector or host cell as described herein. In certain embodiments, a kit may comprise buffers, enzymes, labels, substrates, beads or other surfaces to which the antibodies of the invention are attached, and the like, and instructions for use.

EXAMPLES

Example 1

Production and Humanization of Anti-IL-6R Antibodies

Four New Zealand white rabbits were immunized subcutaneously with 0.4 mg of recombinant human IL-6R-extracellular domain (ECD) in complete Freund's adjuvant (Sigma-Aldrich). After the initial immunization, animals were boosted 5 times with 0.2 mg IL-6R in incomplete Freund's adjuvant in a 3 week-interval. The rabbit with the highest serum titers and IL-6R-ECD neutralizing activity was intravenously boosted with 0.4 mg IL-6R-ECD in PBS four days before splenectomy for cell fusion.

Antibody Generation

Splenocytes were harvested from the immunized rabbit and fused with rabbit plasmacytoma cells 240E-W2 using PEG4000 (Sigma Chemical, St. Louis, Mo.). After being selected by HAT (hypoxanthine, aminopterin, and thymidine), hybridoma clones growing in the original 96-well plates were transferred to new 96-well plates with a medium change. Hybridoma supernatants were collected and screened for specific binding to IL-6R-ECD in a direct ELISA. Five hundred seventy-two hybridomas that were positive in the ELISA binding assay were selected for functional screening.

Functional Screening of Hybridomas

For functional screening, the supernatant from the confirmed 572 positive clones in 24-well plates were tested for neutralizing IL-6R/IL-6 binding by ELISA. These experiments identified 25 unique positive clones which were further tested for neutralization of IL-6 induced TF-1 cell (human premyeloid cell line) proliferation. Sixteen clones were found to neutralize IL-6 activity. The top 10 clones that neutralized IL-6 activity were further selected for molecular cloning and recombinant expression for further functional characterization.

Recombinant Anti-IL-6R Antibodies

DNA fragments of L chains and the variable region (VH) of H chains of rabbit IgG from the top 10 clones were amplified by PCR. The L chain fragment was cloned into pTT5 vector at Hind III and Not I sites and the VH fragment into the constant region of H chain built-in pTT5 vector at Hind III and Kpn I sites. For each hybridoma, three DNA clones of L or H chain were sequenced and the plasmid with a consensus sequence was identified and used for recombinant expression. To express the recombinant antibody, the L and H chain plasmids were co-transfected into 293-6E cells (National Research Council Canada). The supernatants were harvested 5 days later and quantified using an ELISA assay to measure the IgG concentration before functional assays.

Functional Screening of Recombinant Anti-IL-6R Antibodies

Numerous assays were used to characterize the potency of the top 10 anti-IL-6R antibodies identified above. In particular, the anti-IL-6R antibodies were tested for binding to IL-6R on U266B1 cells expressing IL-6R, for ability to block receptor-ligand binding in an ELISA, for their ability to inhibit IL-6-induced TF-1 cell growth, and for their ability to inhibit STAT-3 phosphorylation. The results from these studies are summarized in Table 1 below.

TABLE 1

Summary of Top 10 clones

| # Clone | Direct ELISA EC50 ug/ml | FACS binding EC50 ng/ml | RL-ELISA IC50 ug/ml | TF-1 proliferation IC50 ug/ml | STAT3 phosphorylation Inhibition |
|---|---|---|---|---|---|
| # 5 | 0.04 | 26.11 | 0.38 | 0.03 | (++++) |
| # 21 | 0.04 | 32.55 | 0.47 | 0.11 | (+) |
| # 23 | 0.07 | 26.26 | 0.38 | 0.07 | (+) |
| # 36 | 0.02 | 20.29 | 0.23 | 0.04 | (++++++++) |
| # 37 | 0.05 | 33.12 | 0.39 | 0.09 | (+) |
| # 40 | 0.02 | 57.31 | 1.36 | 0.02 | (+) |
| # 42 | 0.04 | 96.06 | 0.34 | 0.03 | (+) |
| # 51 | 0.03 | 68.73 | 0.80 | 0.02 | (+++++) |
| R #5 | 0.04 | 41.08 | 0.26 | 0.09 | (++) |
| R #15 | 0.07 | 178.00 | 0.43 | 0.19 | (+) |
| hPM-1 (benchmark) | | 206.20 | 0.56 | 0.04 | (+) |

The amino acid sequences for the VH and VL regions of the top 10 clones summarized in Table 1 are provided in SEQ ID Nos: 25-34 and 35-44, respectively. FIG. 2 shows an alignment of the amino acid sequences of the VH and VL. The CDRs are underlined. The amino acid sequences of the VHCDR1, VHCDR2 and VHCDR3 for all of the clones are provided in SEQ ID Nos:45-74. The amino acid sequences of the VLCDR1, VLCDR2 and VLCDR3 for all of the clones are provided in SEQ ID Nos:75-104.

Of note were clones #36 and #51, and in particular clone #36, which had >10 fold higher inhibition of STAT3 phosphorylation as compared to tocilizumab (hPM-1). The top two candidates, clones #36 and #51 were selected for humanization and further characterization.

Humanization Design

Clones #36 and #51 were humanized by grafting CDRs to human germline frame. First, the heavy chain (VH) and light chain (VK) variable region sequences of clones 36 and 51 were blasted against the human germline VH and VK database. The closest human germline sequences, VH3-66 and VK-A20 (clone 36) and VK-L12 (clone 51) were identified as the template for humanization. Secondly, the rabbit residues in the framework regions potentially involved in CDR contacts or inter-chain contacts were identified based on knowledge from human and rabbit antibodies. Residues considered not critical to the structural activity of the antibodies were identified based on knowledge from previous humanized rabbit antibodies. After humanization, the frameworks of the humanized #36 and #51 are 92.35% and 91.8% identical, respectively, to the human germline frameworks. The amino acid sequences of the humanized VH and VL regions for clone #36 are set forth in SEQ ID NOs:9 and 10, respectively. The amino acid sequences of the humanized VH and VL regions for clone #51 are set forth in SEQ ID NOs:19 and 20, respectively.

Expression of Humanized Clone #36 and #51

DNA encoding humanized VK and VH of clones #36 and #51 was synthesized by MCLab (South San Francisco, Calif., USA). The DNA fragments include signal peptide and a Kozak sequence at the 5' end. To express the humanized version of #36 and #51, the humanized VK fragment was cloned into human CK built-in pTT5 vector at Hind III and Nhe I. The humanized VH was cloned into human IgG1 CH built-in pTT5 vector at Hind III and BsiW I site. DNA and amino acid sequences of human CK (SEQ ID NOs:24 and 23, respectively) and IgG1 CH (SEQ ID NOs:22 and 21, respectively) were chosen for the constant region. Humanized versions of #36 and #51 were expressed in 293-6E cells, purified through a protein A column and quantified by UV280 after dialyzing against PBS buffer.

Functional Screening of Humanized Candidate Anti-IL-6R Antibodies #36 and #51

Numerous assays were used to characterize the potency of the #36 and #51 humanized candidate anti-IL-6R antibodies identified above. In particular, the rabbit anti-IL-6R antibodies and their humanized counterparts were tested for binding to IL-6R on U266B1 cells expressing IL-6R, for ability to block receptor-ligand binding in an ELISA, for their ability to inhibit IL-6-induced TF-1 cell growth, and for their ability to inhibit STAT-3 phosphorylation. The results of these experiments are shown in FIG. 1 and are summarized in Table 2 below and indicated that the top 2 humanized anti-IL-6R lead antibodies retain most of their activity. Clone #51 was shown to be slightly less good at blocking receptor-ligand binding. The results indicated that Clone #36 is 6-times more potent than benchmark Tocilizumab in ligand-receptor binding assays and is 6-10 times more potent in inhibiting phosphorylation of STAT3, qualifying this humanized anti-IL-6R antibody as "bio-better".

TABLE 2

Summary of Humanized Anti-IL-6R Antibody Leads

| Clone | Direct ELISA EC50 ug/ml | FACS binding EC50 ug/ml | RL-ELISA IC50 ug/ml | TF-1 proliferation IC50 ug/ml |
|---|---|---|---|---|
| 36 | 0.05953 | 0.0776 | 0.2347 | 0.1625 |
| Humanized 36 | 0.02157 | 0.1446 | 0.3903 | 0.1815 |
| 51 | 2.18E-09 | 0.1644 | 0.2878 | 0.1541 |
| Humanized 51 | 0.01693 | 0.3556 | 0.26 | 1.061 |
| Tocilizumab | 0.04576 | 0.6016 | 1.099 | 0.2137 |

Antigen binding affinities of the lead humanized anti-IL-6R antibodies were measured by surface Plasmon resonance (SPR). The Kd of each antibody is shown in Table 3. Humanized clones had equal or better KD than Tocilizumab with humanized clone #36 showing higher binding affinity to IL-6R than clone #51.

TABLE 3

Humanized Anti-IL-6R Antibody Leads Have Equal or Better KD than Benchmark

| Clone | $k_a$ (1/Ms) | $k_d$ (1/s) | $K_D$ (nM) | Chi$^2$ |
|---|---|---|---|---|
| 5 | 5.33E5 | 2.79E-4 | 0.523 | 0.182 |
| R5 | 4.11E5 | 7.23E-4 | 1.76 | 0.252 |
| 36 | 5.38E5 | 3.42E-4 | 0.635 | 0.241 |
| 51 | 3.93E5 | 4.63E-4 | 1.17 | 0.404 |
| humanized 36 | 5.89E5 | 3.1 E-4 | 0.526 | 0.246 |
| humanized 51 | 3.11E5 | 4E-4 | 1.29 | 0.114 |
| Tocilizumab | 2.52 E5 | 9.7 E-4 | 3.85 | 0.172 |

Candidate Anti-IL-6R Antibodies #36 and #51 Cross-Reactivity

Human and monkey IL-6R share 97.3% identity in the ECD. Experiments showed that clone #36 and #51 do not cross-react with mouse IL-6R, but recognize rhesus macaque (*Macaca mulatta*) IL-6R. Accordingly, these candidates can be used in collagen-induced arthritis in monkeys, a well-accepted and relevant animal model for arthritis.

The various embodiments described above can be combined to provide further embodiments. All of the U.S.

patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated antibody or antigen-binding fragment thereof that binds to human interleukin-6 receptor (IL-6R), comprising:
   (a) a heavy chain variable region comprising a VHCDR1 region comprising the amino acid sequence set forth in SEQ ID NO:13, a VHCDR2 region comprising the amino acid sequence set forth in SEQ ID NO:14, and a VHCDR3 region comprising the amino acid sequence set forth in SEQ ID NO:15, and a light chain variable region comprising a VLCDR1 region comprising the amino acid sequence set forth in SEQ ID NO:16, a VLCDR2 region comprising the amino acid sequence set forth in SEQ ID NO: 17, and a VLCDR3 region comprising the amino acid sequence set forth in SEQ ID NO:18;
   (b) a heavy chain variable region comprising a VHCDR1 region comprising the amino acid sequence set forth in SEQ ID NO:45, a VHCDR2 region comprising the amino acid sequence set forth in SEQ ID NO:55, and a VHCDR3 region comprising the amino acid sequence set forth in SEQ ID NO:65, and a light chain variable region comprising a VLCDR1 region comprising the amino acid sequence set forth in SEQ ID NO:75, a VLCDR2 region comprising the amino acid sequence set forth in SEQ ID NO:85, and a VLCDR3 region comprising the amino acid sequence set forth in SEQ ID NO:95;
   (c) a heavy chain variable region comprising a VHCDR1 region comprising the amino acid sequence set forth in SEQ ID NO:50, a VHCDR2 region comprising the amino acid sequence set forth in SEQ ID NO:60, and a VHCDR3 region comprising the amino acid sequence set forth in SEQ ID NO:70, and a light chain variable region comprising a VLCDR1 region comprising the amino acid sequence set forth in SEQ ID NO:80, a VLCDR2 region comprising the amino acid sequence set forth in SEQ ID NO:90, and a VLCDR3 region comprising the amino acid sequence set forth in SEQ ID NO:100; or
   (d) a heavy chain variable region comprising a VHCDR1 region comprising the amino acid sequence set forth in SEQ ID NO:51, a VHCDR2 region comprising the amino acid sequence set forth in SEQ ID NO:61, and a VHCDR3 region comprising the amino acid sequence set forth in SEQ ID NO:71, and a light chain variable region comprising a VLCDR1 region comprising the amino acid sequence set forth in SEQ ID NO:81, a VLCDR2 region comprising the amino acid sequence set forth in SEQ ID NO:91, and a VLCDR3 region comprising the amino acid sequence set forth in SEQ ID NO: 101.

2. The isolated antibody or antigen-binding fragment thereof of claim 1 wherein the heavy chain variable region comprises the amino acid sequence set forth in SEQ ID NO:19.

3. The isolated antibody or antigen-binding fragment thereof of claim 1 wherein the light chain variable region comprises the amino acid sequence set forth in SEQ ID NO:20.

4. The isolated antibody or antigen-binding fragment thereof of claim 1, wherein the antibody is humanized.

5. The isolated antibody or antigen-binding fragment thereof of claim 1, wherein the antibody is selected from the group consisting of a single chain antibody, an scFv, a univalent antibody lacking a hinge region, and a minibody.

6. The isolated antigen-binding fragment of claim 1, wherein the antigen-binding fragment is a Fab or a Fab' fragment.

7. The isolated antigen-binding fragment of claim 1, wherein the antigen-binding fragment is a F(ab')2 fragment.

8. The isolated antibody of claim 1, wherein the antibody is a whole antibody.

9. The isolated antibody or antigen-binding fragment thereof of claim 1, comprising a human IgG constant domain.

10. The isolated antibody or antigen-binding fragment thereof of claim 9, wherein the IgG constant domain comprises an IgG1 CH1 domain.

11. The isolated antibody or antigen-binding fragment thereof of claim 9 wherein the IgG constant domain comprises an IgG1 Fc region.

12. A composition comprising a physiologically acceptable carrier and a therapeutically effective amount of the isolated antibody or antigen-binding fragment thereof according to claim 1.

13. The isolated antibody or antigen-binding fragment thereof of claim 1, wherein the heavy chain variable region comprises the VHCDR1 region comprising the amino acid sequence set forth in SEQ ID NO:13, the VHCDR2 region comprising the amino acid sequence set forth in SEQ ID NO: 14, and the VHCDR3 region comprising the amino acid sequence set forth in SEQ ID NO:15, and wherein the light chain variable region comprises the VLCDR1 region comprising the amino acid sequence set forth in SEQ ID NO:16, the VLCDR2 region comprising the amino acid sequence set forth in SEQ ID NO:17, and the VLCDR3 region comprising the amino acid sequence set forth in SEQ ID NO: 18.

14. The isolated antibody or antigen-binding fragment thereof of claim 1, wherein the heavy chain variable region comprises the amino acid sequence set forth in SEQ ID NO:19 and the light chain variable region comprises the amino acid sequence set forth in SEQ ID NO:20.

15. The isolated antibody or antigen-binding fragment thereof of claim 1, wherein the heavy chain variable region comprises the VHCDR1 region comprising the amino acid sequence set forth in SEQ ID NO:45, the VHCDR2 region comprising the amino acid sequence set forth in SEQ ID NO:55, and the VHCDR3 region comprising the amino acid sequence set forth in SEQ ID NO:65, and wherein the light chain variable region comprises the VLCDR1 region comprising the amino acid sequence set forth in SEQ ID NO:75, the VLCDR2 region comprising the amino acid sequence set forth in SEQ ID NO:85, and the VLCDR3 region comprising the amino acid sequence set forth in SEQ ID NO:95.

16. The isolated antibody or antigen-binding fragment thereof of claim 1, wherein the heavy chain variable region comprises the VHCDR1 region comprising the amino acid sequence set forth in SEQ ID NO:50, the VHCDR2 region comprising the amino acid sequence set forth in SEQ ID NO:60, and the VHCDR3 region comprising the amino acid sequence set forth in SEQ ID NO:70, and wherein the light chain variable region comprises the VLCDR1 region comprising the amino acid sequence set forth in SEQ ID NO:80, the VLCDR2 region comprising the amino acid sequence set forth in SEQ ID NO:90, and the VLCDR3 region comprising the amino acid sequence set forth in SEQ ID NO: 100.

17. The isolated antibody or antigen-binding fragment thereof of claim 1, wherein the heavy chain variable region comprises the VHCDR1 region comprising the amino acid sequence set forth in SEQ ID NO:51, the VHCDR2 region comprising the amino acid sequence set forth in SEQ ID NO:61, and the VHCDR3 region comprising the amino acid sequence set forth in SEQ ID NO:71, and wherein the light chain variable region comprises the VLCDR1 region comprising the amino acid sequence set forth in SEQ ID NO:81, the VLCDR2 region comprising the amino acid sequence set forth in SEQ ID NO:91, and the VLCDR3 region comprising the amino acid sequence set forth in SEQ ID NO: 101.

* * * * *

SEQUENCE LISTING

```
<160> NUMBER OF SEQ ID NOS: 107

<210> SEQ ID NO 1
<211> LENGTH: 117
<212> TYPE: PRT
<213> ORGANISM: Oryctolagus cuniculus

<400> SEQUENCE: 1

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Tyr
            20                  25                  30

Met Ser Trp Val Arg Gln Ala Pro Gly Lys Gly Leu Glu Trp Ile Gly
        35                  40                  45

Ile Thr Thr Thr Ser Thr Asn Thr Phe Tyr Ala Ser Trp Ala Lys Gly
    50                  55                  60

Arg Phe Thr Ile Ser Lys Thr Ser Ala Thr Val Asp Leu Lys Ile Thr
65                  70                  75                  80

Ser Pro Thr Ile Glu Asp Thr Ala Thr Tyr Phe Cys Ala Arg Tyr Gly
                85                  90                  95

Gly Asn Ser Ala Tyr Tyr Ala Phe Ser Leu Trp Gly Gln Gly Thr Leu
            100                 105                 110

Val Thr Val Ser Ser
        115

<210> SEQ ID NO 2
<211> LENGTH: 109
<212> TYPE: PRT
<213> ORGANISM: Oryctolagus cuniculus

<400> SEQUENCE: 2

Gln Val Leu Thr Gln Thr Ala Ser Ser Val Ser Ala Ala Val Gly Gly
1               5                   10                  15

Thr Val Thr Ile Ser Cys Gln Ser Ser Gln Ser Val Tyr Asn Asn Asn
            20                  25                  30

Tyr Leu Ala Trp Phe Gln Gln Lys Pro Gly Gln Pro Pro Lys Leu Leu
        35                  40                  45

Ile Tyr Gly Ala Ser Asn Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asn Ala Ala Thr Tyr Tyr Cys Gln Gly Tyr Tyr Asn Gly Val
                85                  90                  95

Ile Phe Val Phe Gly Gly Gly Thr Glu Val Val Val Lys
            100                 105

<210> SEQ ID NO 3
<211> LENGTH: 5
<212> TYPE: PRT
<213> ORGANISM: Oryctolagus cuniculus
```

```
<400> SEQUENCE: 3

Ser Tyr Tyr Met Ser
1               5

<210> SEQ ID NO 4
<211> LENGTH: 16
<212> TYPE: PRT
<213> ORGANISM: Oryctolagus cuniculus

<400> SEQUENCE: 4

Ile Thr Thr Thr Ser Thr Asn Thr Phe Tyr Ala Ser Trp Ala Lys Gly
1               5                   10                  15

<210> SEQ ID NO 5
<211> LENGTH: 12
<212> TYPE: PRT
<213> ORGANISM: Oryctolagus cuniculus

<400> SEQUENCE: 5

Tyr Gly Gly Asn Ser Ala Tyr Tyr Ala Phe Ser Leu
1               5                   10

<210> SEQ ID NO 6
<211> LENGTH: 13
<212> TYPE: PRT
<213> ORGANISM: Oryctolagus cuniculus

<400> SEQUENCE: 6

Gln Ser Ser Gln Ser Val Tyr Asn Asn Asn Tyr Leu Ala
1               5                   10

<210> SEQ ID NO 7
<211> LENGTH: 7
<212> TYPE: PRT
<213> ORGANISM: Oryctolagus cuniculus

<400> SEQUENCE: 7

Gly Ala Ser Asn Leu Ala Ser
1               5

<210> SEQ ID NO 8
<211> LENGTH: 10
<212> TYPE: PRT
<213> ORGANISM: Oryctolagus cuniculus

<400> SEQUENCE: 8

Gln Gly Tyr Tyr Asn Gly Val Ile Phe Val
1               5                   10

<210> SEQ ID NO 9
<211> LENGTH: 120
<212> TYPE: PRT
<213> ORGANISM: Artificial Sequence
<220> FEATURE:
<223> OTHER INFORMATION: Humanized sequence of the VH region of clone 36
      rabbit anti-IL6R antibody

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Tyr Met Ser Trp Val Arg Gln Ala Pro Gly Lys Gly Leu Glu Trp Ile
```

```
                35                  40                  45
Gly Ile Thr Thr Thr Ser Thr Asn Thr Phe Tyr Ala Ser Trp Ala Lys
        50                      55                  60

Gly Arg Phe Thr Ile Ser Lys Asp Ser Ser Lys Asn Thr Val Tyr Leu
 65                  70                  75                  80

Gln Met Asn Ser Pro Arg Ala Glu Asp Thr Ala Val Tyr Phe Cys Ala
                 85                  90                  95

Arg Tyr Gly Gly Asn Ser Ala Tyr Tyr Ala Phe Ser Leu Trp Gly Gln
                100                 105                 110

Gly Thr Leu Val Thr Val Ser Ser
        115                 120

<210> SEQ ID NO 10
<211> LENGTH: 110
<212> TYPE: PRT
<213> ORGANISM: Artificial Sequence
<220> FEATURE:
<223> OTHER INFORMATION: Humanized sequence of the VL region of clone 36
      rabbit anti-IL6R antibody

<400> SEQUENCE: 10

Asp Ile Gln Met Thr Gln Ser Pro Ser Ser Leu Ser Ala Ser Val Gly
 1               5                  10                  15

Asp Arg Val Thr Ile Ser Cys Gln Ser Ser Gln Ser Val Tyr Asn Asn
                20                  25                  30

Asn Tyr Leu Ala Trp Phe Gln Gln Lys Pro Gly Lys Pro Pro Lys Leu
        35                  40                  45

Leu Ile Tyr Gly Ala Ser Asn Leu Ala Ser Gly Val Pro Ser Arg Phe
 50                  55                  60

Ser Gly Ser Gly Ser Gly Thr Gln Phe Thr Leu Thr Ile Ser Ser Leu
 65                  70                  75                  80

Gln Pro Glu Asp Val Ala Thr Tyr Tyr Cys Gln Gly Tyr Tyr Asn Gly
                 85                  90                  95

Val Ile Phe Val Phe Gly Gly Gly Thr Lys Val Glu Ile Lys
                100                 105                 110

<210> SEQ ID NO 11
<211> LENGTH: 117
<212> TYPE: PRT
<213> ORGANISM: Oryctolagus cuniculus

<400> SEQUENCE: 11

Gln Ser Val Glu Glu Ser Gly Gly Arg Leu Val Thr Pro Gly Thr Pro
 1               5                  10                  15

Leu Thr Leu Thr Cys Thr Ala Ser Gly Phe Asp Ile Ser Ser Tyr Ser
                20                  25                  30

Leu Gln Trp Val Arg Gln Ser Pro Gly Lys Gly Leu Glu Tyr Ile Gly
        35                  40                  45

Phe Ile Arg Pro Asp Gly Ser Ala His Tyr Ala Thr Trp Ala Lys Gly
 50                  55                  60

Arg Phe Thr Ile Ser Lys Thr Ser Ser Thr Thr Val Asp Leu Lys Met
 65                  70                  75                  80

Thr Ser Leu Thr Thr Glu Asp Thr Ala Thr Tyr Phe Cys Ala Arg Asp
                 85                  90                  95

Asp Ile Ser Ser Asp Tyr Phe Pro Asn Leu Trp Gly Pro Gly Thr Leu
                100                 105                 110

Val Thr Val Ser Ser
```

-continued

115

<210> SEQ ID NO 12
<211> LENGTH: 109
<212> TYPE: PRT
<213> ORGANISM: Oryctolagus cuniculus

<400> SEQUENCE: 12

Gln Val Leu Thr Gln Thr Pro Ser Pro Val Ser Ala Ala Val Gly Gly
1               5                   10                  15

Thr Val Thr Ile Ser Cys Gln Ala Ser Glu Ser Val Tyr Asn Lys Asn
            20                  25                  30

Asn Leu Ala Trp Tyr Gln Gln Lys Pro Gly Gln Pro Pro Lys Leu Leu
        35                  40                  45

Ile Tyr Asp Ala Ser Asp Leu Ala Ser Gly Val Ser Ser Arg Phe Lys
    50                  55                  60

Gly Ser Gly Ser Gly Thr Gln Phe Thr Leu Thr Ile Ser Asp Leu Glu
65                  70                  75                  80

Cys Ala Asp Ala Ala Thr Tyr Tyr Cys Ala Gly Gly Ser Gly Asn
                85                  90                  95

Val Tyr Asp Phe Gly Gly Gly Thr Glu Val Val Val Lys
            100                 105

<210> SEQ ID NO 13
<211> LENGTH: 5
<212> TYPE: PRT
<213> ORGANISM: Oryctolagus cuniculus

<400> SEQUENCE: 13

Ser Tyr Ser Leu Gln
1               5

<210> SEQ ID NO 14
<211> LENGTH: 16
<212> TYPE: PRT
<213> ORGANISM: Oryctolagus cuniculus

<400> SEQUENCE: 14

Phe Ile Arg Pro Asp Gly Ser Ala His Tyr Ala Thr Trp Ala Lys Gly
1               5                   10                  15

<210> SEQ ID NO 15
<211> LENGTH: 11
<212> TYPE: PRT
<213> ORGANISM: Oryctolagus cuniculus

<400> SEQUENCE: 15

Asp Asp Ile Ser Ser Asp Tyr Phe Pro Asn Leu
1               5                   10

<210> SEQ ID NO 16
<211> LENGTH: 13
<212> TYPE: PRT
<213> ORGANISM: Oryctolagus cuniculus

<400> SEQUENCE: 16

Gln Ala Ser Glu Ser Val Tyr Asn Lys Asn Asn Leu Ala
1               5                   10

<210> SEQ ID NO 17
<211> LENGTH: 7
<212> TYPE: PRT

<213> ORGANISM: Oryctolagus cuniculus

<400> SEQUENCE: 17

Asp Ala Ser Asp Leu Ala Ser
1               5

<210> SEQ ID NO 18
<211> LENGTH: 10
<212> TYPE: PRT
<213> ORGANISM: Oryctolagus cuniculus

<400> SEQUENCE: 18

Ala Gly Gly Gly Ser Gly Asn Val Tyr Asp
1               5                   10

<210> SEQ ID NO 19
<211> LENGTH: 119
<212> TYPE: PRT
<213> ORGANISM: Artificial Sequence
<220> FEATURE:
<223> OTHER INFORMATION: Humanized sequence of the VH region of clone 51
      rabbit anti-IL6R antibody

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Ile Ser Ser Tyr
            20                  25                  30

Ser Leu Gln Trp Val Arg Gln Ser Pro Gly Lys Gly Leu Glu Tyr Ile
        35                  40                  45

Gly Phe Ile Arg Pro Asp Gly Ser Ala His Tyr Ala Thr Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Asp Asp Ile Ser Ser Asp Tyr Phe Pro Asn Leu Trp Gly Pro Gly
            100                 105                 110

Thr Leu Val Thr Val Ser Ser
        115

<210> SEQ ID NO 20
<211> LENGTH: 110
<212> TYPE: PRT
<213> ORGANISM: Artificial Sequence
<220> FEATURE:
<223> OTHER INFORMATION: Humanized sequence of the VL region of clone 51
      rabbit anti-IL6R antibody

<400> SEQUENCE: 20

Asp Ile Gln Met Thr Gln Ser Pro Ser Thr Leu Ser Ala Ser Val Gly
1               5                   10                  15

Asp Arg Val Thr Ile Ser Cys Gln Ala Ser Glu Ser Val Tyr Asn Lys
            20                  25                  30

Asn Asn Leu Ala Trp Tyr Gln Gln Lys Pro Gly Lys Pro Pro Lys Leu
        35                  40                  45

Leu Ile Tyr Asp Ala Ser Asp Leu Ala Ser Gly Val Pro Ser Arg Phe
    50                  55                  60

Ser Gly Ser Gly Ser Gly Thr Gln Phe Thr Leu Thr Ile Ser Ser Leu
65                  70                  75                  80

```
Gln Pro Asp Asp Phe Ala Thr Tyr Tyr Cys Ala Gly Gly Ser Gly
                 85                  90                  95

Asn Val Tyr Asp Phe Gly Gly Thr Lys Val Glu Ile Lys
            100                 105                 110

<210> SEQ ID NO 21
<211> LENGTH: 330
<212> TYPE: PRT
<213> ORGANISM: Homo sapiens

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 22
```

<211> LENGTH: 993
<212> TYPE: DNA
<213> ORGANISM: Homo sapiens

<400> SEQUENCE: 22

| | | | | | |
|---|---|---|---|---|---|
| gctagcacca | agggcccatc | ggtcttcccc | ctggcaccct | cctccaagag | cacctctggg | 60 |
| ggcacagcgg | ccctgggctg | cctggtcaag | gactacttcc | ccgaaccggt | gacggtgtcg | 120 |
| tggaactcag | gcgccctgac | cagcggcgtg | cacaccttcc | cggctgtcct | acagtcctca | 180 |
| ggactctact | ccctcagcag | cgtggtgacc | gtgccctcca | gcagcttggg | cacccagacc | 240 |
| tacatctgca | acgtgaatca | caagcccagc | aacaccaagg | tggacaagaa | agttgagccc | 300 |
| aaatcttgtg | acaaaactca | cacatgccca | ccgtgcccag | cacctgaact | cctgggggga | 360 |
| ccgtcagtct | tcctcttccc | cccaaaaccc | aaggacaccc | tcatgatctc | ccggacccct | 420 |
| gaggtcacat | gcgtggtggt | ggacgtgagc | cacgaagacc | ctgaggtcaa | gttcaactgg | 480 |
| tacgtggacg | gcgtggaggt | gcataatgcc | aagacaaagc | cgcgggagga | gcagtacaac | 540 |
| agcacgtacc | gtgtggtcag | cgtcctcacc | gtcctgcacc | aggactggct | gaatggcaag | 600 |
| gagtacaagt | gcaaggtctc | caacaaagcc | ctcccagccc | ccatcgagaa | aaccatctcc | 660 |
| aaagccaaag | ggcagccccg | agaaccacag | gtgtacaccc | tgcccccatc | ccgggatgag | 720 |
| ctgaccaaga | accaggtcag | cctgacctgc | ctggtcaaag | gcttctatcc | cagcgacatc | 780 |
| gccgtggagt | gggagagcaa | tgggcagccg | gagaacaact | acaagaccac | gcctcccgtg | 840 |
| ctggactccg | acggctcctt | cttcctctac | agcaagctca | ccgtggacaa | gagcaggtgg | 900 |
| cagcagggga | acgtcttctc | atgctccgtg | atgcatgagg | ctctgcacaa | ccactacacg | 960 |
| cagaagagcc | tctccctgtc | tccgggtaaa | taa | | | 993 |

<210> SEQ ID NO 23
<211> LENGTH: 107
<212> TYPE: PRT
<213> ORGANISM: Homo sapiens

<400> SEQUENCE: 23

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 24
<211> LENGTH: 324
<212> TYPE: DNA
<213> ORGANISM: Homo sapiens

<400> SEQUENCE: 24

| | | | | | |
|---|---|---|---|---|---|
| cgtacggtgg | ctgcaccatc | tgtcttcatc | ttcccgccat | ctgatgagca | gttgaaatct | 60 |

```
ggaactgcct ctgttgtgtg cctgctgaat aacttctatc ccagagaggc caaagtacag      120
tggaaggtgg ataacgccct ccaatcgggt aactcccagg agagtgtcac agagcaggac      180
agcaaggaca gcacctacag cctcagcagc accctgacgc tgagcaaagc agactacgag      240
aaacacaaag tctacgcctg cgaagtcacc catcagggcc tgagctcgcc cgtcacaaag      300
agcttcaaca ggggagagtg ttag                                              324

<210> SEQ ID NO 25
<211> LENGTH: 135
<212> TYPE: PRT
<213> ORGANISM: Oryctolagus cuniculus

<400> SEQUENCE: 25

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Arg Tyr Trp Met Ser Trp Val Arg Gln Ala Pro Gly Lys Gly Leu Glu
    50                  55                  60

Trp Ile Gly Met Ile Ser Gly Asn Thr Trp Tyr Ala Ser Trp Ala
65                  70                  75                  80

Lys Gly Arg Phe Thr Ile Ser Lys Thr Ser Thr Thr Val Asp Leu Lys
                85                  90                  95

Ile Thr Ser Pro Thr Thr Glu Asp Thr Ala Thr Tyr Phe Cys Ala Arg
            100                 105                 110

Gly Ile Asp Thr Gly Ile Ala Thr Thr Phe Asn Leu Trp Gly Pro Gly
        115                 120                 125

Thr Leu Val Thr Val Ser Ser
    130                 135

<210> SEQ ID NO 26
<211> LENGTH: 136
<212> TYPE: PRT
<213> ORGANISM: Oryctolagus cuniculus

<400> SEQUENCE: 26

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Asn Tyr Tyr Met Ser Trp Val Arg Gln Ala Pro Gly Lys Gly Leu Glu
    50                  55                  60

Trp Ile Gly Ile Ser Ser Thr Ser Asn Thr Phe Tyr Ala Ser Trp
65                  70                  75                  80

Ala Lys Gly Arg Phe Thr Ile Ser Lys Thr Ser Ala Thr Val Asp Leu
                85                  90                  95

Lys Ile Thr Ser Pro Thr Thr Glu Asp Thr Ala Thr Tyr Phe Cys Ala
            100                 105                 110

Arg Tyr Gly Gly Asn Ser Ala Tyr Tyr Ala Phe Ser Leu Trp Gly Gln
        115                 120                 125

Gly Thr Leu Val Thr Val Ser Ser
    130                 135
```

<210> SEQ ID NO 27
<211> LENGTH: 135
<212> TYPE: PRT
<213> ORGANISM: Oryctolagus cuniculus

<400> SEQUENCE: 27

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Arg Tyr Trp Met Ser Trp Val Arg Gln Ala Pro Gly Lys Gly Leu Glu
    50                  55                  60

Trp Ile Gly Met Ile Ser Gly Gly Asn Thr Trp Tyr Ala Ser Trp Ala
65                  70                  75                  80

Lys Gly Arg Phe Thr Ile Ser Lys Thr Ser Thr Thr Val Asp Leu Lys
                85                  90                  95

Ile Thr Ser Pro Thr Thr Glu Asp Thr Ala Thr Tyr Phe Cys Ala Arg
            100                 105                 110

Gly Ile Asp Thr Gly Ile Ala Thr Thr Phe Asn Leu Trp Gly Pro Gly
        115                 120                 125

Thr Leu Val Thr Val Ser Ser
    130                 135

<210> SEQ ID NO 28
<211> LENGTH: 136
<212> TYPE: PRT
<213> ORGANISM: Oryctolagus cuniculus

<400> SEQUENCE: 28

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Tyr Met Ser Trp Val Arg Gln Ala Pro Gly Lys Gly Leu Glu
    50                  55                  60

Trp Ile Gly Ile Thr Thr Thr Ser Thr Asn Thr Phe Tyr Ala Ser Trp
65                  70                  75                  80

Ala Lys Gly Arg Phe Thr Ile Ser Lys Thr Ser Ala Thr Val Asp Leu
                85                  90                  95

Lys Ile Thr Ser Pro Thr Ile Glu Asp Thr Ala Thr Tyr Phe Cys Ala
            100                 105                 110

Arg Tyr Gly Gly Asn Ser Ala Tyr Tyr Ala Phe Ser Leu Trp Gly Gln
        115                 120                 125

Gly Thr Leu Val Thr Val Ser Ser
    130                 135

<210> SEQ ID NO 29
<211> LENGTH: 135
<212> TYPE: PRT
<213> ORGANISM: Oryctolagus cuniculus

<400> SEQUENCE: 29

```
Met Glu Thr Gly Leu Arg Trp Leu Leu Leu Val Ala Val Leu Lys Gly
 1               5                  10                  15

Val Gln Cys Gln Ser Leu Glu Glu Ser Gly Gly Arg Leu Val Thr Pro
             20                  25                  30

Gly Thr Pro Leu Thr Leu Thr Cys Thr Val Ser Gly Ile Asp Leu Ser
             35                  40                  45

Arg Tyr Trp Met Ser Trp Val Arg Gln Ala Pro Gly Lys Gly Leu Glu
     50                  55                  60

Trp Ile Gly Met Ile Ser Gly Gly Asn Thr Trp Tyr Ala Ser Trp Ala
 65                  70                  75                  80

Lys Gly Arg Phe Thr Ile Ser Gly Thr Ser Thr Val Asp Leu Lys
                 85                  90                  95

Ile Ile Ser Pro Thr Thr Ala Asp Thr Ala Thr Tyr Phe Cys Ala Arg
             100                 105                 110

Gly Ile Asp Thr Gly Ile Ala Thr Thr Phe Asn Leu Trp Gly Pro Gly
             115                 120                 125

Thr Leu Val Thr Val Ser Ser
             130                 135

<210> SEQ ID NO 30
<211> LENGTH: 141
<212> TYPE: PRT
<213> ORGANISM: Oryctolagus cuniculus

<400> SEQUENCE: 30

Met Glu Thr Gly Leu Arg Trp Leu Leu Leu Val Ala Val Leu Lys Gly
 1               5                  10                  15

Val Gln Cys Gln Ser Leu Glu Glu Ser Gly Gly Arg Leu Val Ser Pro
             20                  25                  30

Gly Gly Ser Leu Thr Leu Thr Cys Thr Val Ser Gly Val Asp Leu Asn
             35                  40                  45

Thr Tyr Ala Met Gly Trp Val Arg Gln Ala Pro Gly Lys Gly Leu Glu
     50                  55                  60

Cys Ile Gly Val Ile Leu Gly Ser Gly Thr Thr Tyr Tyr Ala Asn Trp
 65                  70                  75                  80

Ala Lys Gly Arg Phe Thr Ile Ser Lys Thr Ser Ser Thr Thr Val Asp
                 85                  90                  95

Leu Lys Met Thr Asn Leu Thr Ala Ala Asp Thr Ala Thr Tyr Phe Cys
             100                 105                 110

Ala Gly Asp Arg Tyr Gly Ser Leu Glu Glu Val Ile Thr Pro Tyr Phe
             115                 120                 125

Asp Leu Trp Gly Pro Gly Ile Leu Val Thr Val Ser Ser
     130                 135                 140

<210> SEQ ID NO 31
<211> LENGTH: 133
<212> TYPE: PRT
<213> ORGANISM: Oryctolagus cuniculus

<400> SEQUENCE: 31

Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Thr Pro
             20                  25                  30

Gly Thr Pro Leu Thr Leu Thr Cys Thr Val Ser Gly Phe Ser Leu Ser
             35                  40                  45
```

```
Asn Tyr Trp Met Ser Trp Val Arg Gln Ala Pro Gly Lys Gly Leu Glu
    50                  55                  60

Trp Ile Ala Phe Ile Gly Gly Gly Asn Thr Phe Tyr Ala Ser Trp Ala
65                  70                  75                  80

Lys Gly Arg Phe Thr Ile Ser Lys Thr Ser Thr Thr Val Asp Leu
                85                  90                  95

Ser Met Pro Ser Pro Thr Thr Glu Asp Thr Ala Thr Tyr Phe Cys Ala
                100                 105                 110

Arg Gly Tyr Gly Ala Pro Gly Tyr Asp Leu Trp Gly Gln Gly Thr Leu
                115                 120                 125

Val Thr Val Ser Leu
        130

<210> SEQ ID NO 32
<211> LENGTH: 136
<212> TYPE: PRT
<213> ORGANISM: Oryctolagus cuniculus

<400> SEQUENCE: 32

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
                20                  25                  30

Gly Thr Pro Leu Thr Leu Thr Cys Thr Ala Ser Gly Phe Asp Ile Ser
                35                  40                  45

Ser Tyr Ser Leu Gln Trp Val Arg Gln Ser Pro Gly Lys Gly Leu Glu
    50                  55                  60

Tyr Ile Gly Phe Ile Arg Pro Asp Gly Ser Ala His Tyr Ala Thr Trp
65                  70                  75                  80

Ala Lys Gly Arg Phe Thr Ile Ser Lys Thr Ser Ser Thr Thr Val Asp
                85                  90                  95

Leu Lys Met Thr Ser Leu Thr Thr Glu Asp Thr Ala Thr Tyr Phe Cys
                100                 105                 110

Ala Arg Asp Asp Ile Ser Ser Asp Tyr Phe Pro Asn Leu Trp Gly Pro
                115                 120                 125

Gly Thr Leu Val Thr Val Ser Ser
        130                 135

<210> SEQ ID NO 33
<211> LENGTH: 140
<212> TYPE: PRT
<213> ORGANISM: Oryctolagus cuniculus
<220> FEATURE:
<221> NAME/KEY: VARIANT
<222> LOCATION: (122)..(122)
<223> OTHER INFORMATION: Xaa = Any Amino Acid
<220> FEATURE:
<221> NAME/KEY: VARIANT
<222> LOCATION: (123)..(123)
<223> OTHER INFORMATION: Xaa = Any Amino Acid
<220> FEATURE:
<221> NAME/KEY: VARIANT
<222> LOCATION: (125)..(125)
<223> OTHER INFORMATION: Xaa = Any Amino Acid
<220> FEATURE:
<221> NAME/KEY: VARIANT
<222> LOCATION: (126)..(126)
<223> OTHER INFORMATION: Xaa = Any Amino Acid

<400> SEQUENCE: 33

Met Glu Thr Gly Leu Arg Trp Leu Leu Leu Val Ala Val Leu Lys Gly
1               5                   10                  15
```

-continued

Val Gln Cys Gln Ser Val Glu Ser Gly Gly Arg Leu Val Thr Pro
            20                  25                  30

Gly Thr Pro Leu Thr Val Thr Cys Thr Ala Ser Gly Phe Ser Leu Ser
        35                  40                  45

Thr Tyr Trp Met Ser Trp Val Arg Gln Ala Pro Gly Lys Gly Leu Glu
    50                  55                  60

Trp Ile Gly Met Ile Tyr Gly Asp Ser Asn Asn Lys Phe Tyr Ala Asn
65                  70                  75                  80

Trp Ala Lys Gly Arg Phe Thr Ile Ser Lys Thr Ser Ser Thr Thr Val
                85                  90                  95

Asp Leu Lys Met Thr Ser Leu Thr Thr Glu Asp Thr Ala Thr Tyr Phe
            100                 105                 110

Cys Ala Arg Glu Tyr Phe Ala Asp Ser Xaa Xaa Gly Xaa Xaa Phe Gly
            115                 120                 125

Ile Trp Gly Pro Gly Thr Leu Val Thr Val Ser Ser
    130                 135                 140

<210> SEQ ID NO 34
<211> LENGTH: 137
<212> TYPE: PRT
<213> ORGANISM: Oryctolagus cuniculus
<220> FEATURE:
<221> NAME/KEY: VARIANT
<222> LOCATION: (114)..(114)
<223> OTHER INFORMATION: Xaa = Any Amino Acid
<220> FEATURE:
<221> NAME/KEY: VARIANT
<222> LOCATION: (115)..(115)
<223> OTHER INFORMATION: Xaa = Any Amino Acid
<220> FEATURE:
<221> NAME/KEY: VARIANT
<222> LOCATION: (120)..(120)
<223> OTHER INFORMATION: Xaa = Any Amino Acid
<220> FEATURE:
<221> NAME/KEY: VARIANT
<222> LOCATION: (122)..(122)
<223> OTHER INFORMATION: Xaa = Any Amino Acid

<400> SEQUENCE: 34

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Ile Thr Pro
            20                  25                  30

Gly Gly Ser Leu Thr Leu Thr Cys Thr Val Ser Gly Phe Ser Leu Thr
        35                  40                  45

Thr Tyr Asn Val Ala Trp Val Arg Gln Ala Pro Gly Lys Gly Leu Glu
    50                  55                  60

Trp Ile Gly Ile Ile Gly Gly Thr Gly Asn Thr His Tyr Thr Thr Trp
65                  70                  75                  80

Ala Lys Gly Arg Phe Thr Ile Ser Lys Thr Ser Thr Thr Val Asp Leu
                85                  90                  95

Arg Ile Thr Ser Pro Thr Thr Glu Asp Thr Ala Thr Tyr Phe Cys Ala
            100                 105                 110

Arg Xaa Xaa Leu Gly Gly Gly Xaa Asp Xaa Asp Phe Asp Ile Trp Gly
            115                 120                 125

Pro Gly Thr Leu Val Thr Val Ser Ser
    130                 135

<210> SEQ ID NO 35
<211> LENGTH: 132

<212> TYPE: PRT
<213> ORGANISM: Oryctolagus cuniculus

<400> SEQUENCE: 35

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
            20                  25                  30

Val Ser Ala Ala Val Gly Gly Thr Val Thr Ile Ser Cys Gln Ser Ser
        35                  40                  45

Gln Ser Val Tyr Asn Asn Arg Leu Ser Trp Phe Gln Gln Lys Pro
    50                  55                  60

Gly Gln Pro Pro Lys Leu Leu Ile Tyr Tyr Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Gln Gly Tyr Tyr Ser Gly Val Ile Asn Val Phe Gly Gly Gly Thr Glu
        115                 120                 125

Val Val Val Lys
    130

<210> SEQ ID NO 36
<211> LENGTH: 132
<212> TYPE: PRT
<213> ORGANISM: Oryctolagus cuniculus

<400> SEQUENCE: 36

Met Asp Thr Arg Ala Pro Thr Gln Leu Leu Gly Leu Leu Leu Leu Trp
1               5                   10                  15

Leu Pro Gly Ala Thr Phe Ala Val Val Leu Thr Gln Thr Pro Ser Pro
            20                  25                  30

Val Ser Ala Ala Val Gly Gly Thr Val Thr Ile Asn Cys Gln Ser Ser
        35                  40                  45

Gln Ser Val Tyr Asn Asn Tyr Leu Ala Trp Tyr Gln Gln Lys Pro
    50                  55                  60

Gly Gln Pro Pro Lys Leu Leu Ile Tyr Gly Ala Ser Asn Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Glu Val Gln Cys Asp Asp Ala Ala Thr Tyr Tyr Cys
            100                 105                 110

Gln Gly Tyr Tyr Asn Gly Val Ile Phe Val Phe Gly Gly Gly Thr Glu
        115                 120                 125

Val Val Val Lys
    130

<210> SEQ ID NO 37
<211> LENGTH: 132
<212> TYPE: PRT
<213> ORGANISM: Oryctolagus cuniculus

<400> SEQUENCE: 37

Met Asp Thr Arg Ala Ala Thr Gln Leu Leu Gly Leu Leu Leu Leu Trp
1               5                   10                  15

Leu Pro Gly Ala Thr Phe Ala Gln Val Leu Thr Gln Thr Pro Ser Ser

```
                  20                  25                  30
Val Ser Thr Ala Val Gly Gly Thr Val Thr Ile Ser Cys Gln Ser Ser
            35                  40                  45

Gln Asn Val Tyr Asn Asn Arg Leu Ser Trp Phe Gln Gln Lys Pro
50                  55                  60

Gly Gln Pro Pro Lys Leu Leu Ile Tyr Tyr Thr Ser Thr Leu Pro Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
                100                 105                 110

Gln Gly Tyr Tyr Ser Gly Val Ile Asn Val Phe Gly Gly Gly Thr Glu
            115                 120                 125

Val Val Val Lys
        130

<210> SEQ ID NO 38
<211> LENGTH: 132
<212> TYPE: PRT
<213> ORGANISM: Oryctolagus cuniculus

<400> SEQUENCE: 38

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Ser
                20                  25                  30

Val Ser Ala Ala Val Gly Gly Thr Val Thr Ile Ser Cys Gln Ser Ser
            35                  40                  45

Gln Ser Val Tyr Asn Asn Asn Tyr Leu Ala Trp Phe Gln Gln Lys Pro
50                  55                  60

Gly Gln Pro Pro Lys Leu Leu Ile Tyr Gly Ala Ser Asn Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asn Ala Ala Thr Tyr Tyr Cys
                100                 105                 110

Gln Gly Tyr Tyr Asn Gly Val Ile Phe Val Phe Gly Gly Gly Thr Glu
            115                 120                 125

Val Val Val Lys
        130

<210> SEQ ID NO 39
<211> LENGTH: 132
<212> TYPE: PRT
<213> ORGANISM: Oryctolagus cuniculus

<400> SEQUENCE: 39

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
                20                  25                  30

Val Ser Ala Ala Val Gly Gly Thr Val Thr Ile Ser Cys Gln Ser Ser
            35                  40                  45

Gln Ser Val Tyr Ser Asn Asn Arg Leu Ser Trp Phe Gln Gln Lys Pro
50                  55                  60

Gly Gln Pro Pro Lys Leu Leu Ile Tyr Tyr Thr Ser Thr Leu Ala Ser
```

```
                65                  70                  75                  80
Gly Val Pro Ser Arg Phe Lys Gly Ser Gly Ser Gly Thr Gln Phe Thr
                    85                  90                  95

Leu Thr Ile Ser Asp Leu Glu Cys Asp Asp Ala Ala Thr Tyr Tyr Cys
                100                 105                 110

Gln Gly Tyr Tyr Ser Gly Val Ile Asn Val Phe Gly Gly Gly Thr Glu
                115                 120                 125

Val Val Val Lys
            130

<210> SEQ ID NO 40
<211> LENGTH: 134
<212> TYPE: PRT
<213> ORGANISM: Oryctolagus cuniculus

<400> SEQUENCE: 40

Met Asp Thr Arg Ala Pro Thr Gln Leu Leu Gly Leu Leu Leu Leu Trp
1               5                   10                  15

Leu Pro Gly Ala Arg Cys Ala Asp Val Val Met Thr Gln Thr Pro Ala
                20                  25                  30

Ser Val Glu Ala Ala Val Gly Gly Thr Val Thr Ile Lys Cys Gln Ala
            35                  40                  45

Ser Gln Asn Ile Tyr Asn Asn Leu Ala Trp Tyr Gln Gln Lys Pro Ala
        50                  55                  60

Gln Pro Pro Lys Leu Leu Ile Tyr Ser Ala Ser Thr Leu Glu Ser Gly
65                  70                  75                  80

Val Pro Ser Arg Phe Lys Gly Ser Gly Ser Gly Thr Gly Tyr Thr Leu
                85                  90                  95

Thr Ile Ser Asp Leu Glu Cys Ala Asp Ala Ala Thr Tyr Tyr Cys Gln
                100                 105                 110

Ser Ala Tyr Tyr Thr Ser Tyr Ile Asp His Asn Val Phe Gly Gly Gly
                115                 120                 125

Thr Glu Val Val Val Glu
            130

<210> SEQ ID NO 41
<211> LENGTH: 134
<212> TYPE: PRT
<213> ORGANISM: Oryctolagus cuniculus

<400> SEQUENCE: 41

Met Asp Thr Arg Ala Pro Thr Gln Leu Leu Gly Leu Leu Leu Leu Trp
1               5                   10                  15

Leu Pro Gly Ala Thr Phe Ala Ile Val Met Thr Gln Thr Pro Ser Ser
                20                  25                  30

Lys Ser Val Pro Val Gly Asp Thr Val Thr Ile Asn Cys Gln Ala Ser
            35                  40                  45

Glu Ser Val Tyr Thr Asn Asn Arg Leu Ser Trp Tyr Gln Gln Lys Pro
        50                  55                  60

Gly Gln Pro Pro Lys Leu Leu Ile Tyr Tyr Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Val Val Cys Asp Asn Ala Ala Thr Tyr Tyr Cys
                100                 105                 110

Val Gly Tyr Lys Ser Ser Asp Gly Asp Gly Thr Ala Phe Gly Gly Gly
```

Thr Glu Val Val Val Lys
            130

<210> SEQ ID NO 42
<211> LENGTH: 132
<212> TYPE: PRT
<213> ORGANISM: Oryctolagus cuniculus

<400> SEQUENCE: 42

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Ser Cys Gln Ala Ser
        35                  40                  45

Glu Ser Val Tyr Asn Lys Asn Asn Leu Ala Trp Tyr Gln Gln Lys Pro
    50                  55                  60

Gly Gln Pro Pro Lys Leu Leu Ile Tyr Asp Ala Ser Asp Leu Ala Ser
65                  70                  75                  80

Gly Val Ser Ser Arg Phe Lys Gly Ser Gly Ser Gly Thr Gln Phe Thr
                85                  90                  95

Leu Thr Ile Ser Asp Leu Glu Cys Ala Asp Ala Ala Thr Tyr Tyr Cys
            100                 105                 110

Ala Gly Gly Gly Ser Gly Asn Val Tyr Asp Phe Gly Gly Gly Thr Glu
        115                 120                 125

Val Val Val Lys
            130

<210> SEQ ID NO 43
<211> LENGTH: 132
<212> TYPE: PRT
<213> ORGANISM: Oryctolagus cuniculus

<400> SEQUENCE: 43

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Ser Cys Gln Ser Ser
        35                  40                  45

Gln Ser Val Tyr Lys Asn Asn Tyr Leu Ser Trp Tyr Gln Gln Lys Pro
    50                  55                  60

Gly Gln Pro Pro Lys Leu Leu Ile Tyr Arg Ala Ser Thr Leu Ala Ser
65                  70                  75                  80

Gly Val Ser Ser Arg Phe Lys Gly Ser Gly Ser Gly Thr Gln Phe Thr
                85                  90                  95

Leu Thr Ile Ser Glu Val Gln Cys Asp Asp Ala Ala Thr Tyr Val Cys
            100                 105                 110

Gln Gly Tyr Tyr Ser Gly Pro Ile Tyr Val Phe Gly Gly Gly Thr Glu
        115                 120                 125

Val Val Val Lys
            130

<210> SEQ ID NO 44
<211> LENGTH: 132
<212> TYPE: PRT

<213> ORGANISM: Oryctolagus cuniculus

<400> SEQUENCE: 44

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45

Gln Asn Ile Arg Asn Tyr Leu Ala Trp Tyr Gln Gln Lys Pro Gly Gln
    50                  55                  60

Arg Pro Lys Leu Leu Ile Asp Ala Ala Ala Asn Leu Ala Ser Gly Val
65                  70                  75                  80

Pro Ser Arg Phe Lys Gly Ser Gly Ser Gly Thr Glu Phe Thr Leu Thr
                85                  90                  95

Ile Ser Asp Leu Glu Cys Asp Asp Ala Ala Thr Tyr Tyr Cys Gln Gln
            100                 105                 110

Gly Tyr Ser Val Ile Asn Val Asp Asn Ile Phe Gly Gly Gly Thr Glu
        115                 120                 125

Val Val Val Lys
    130

<210> SEQ ID NO 45
<211> LENGTH: 10
<212> TYPE: PRT
<213> ORGANISM: Oryctolagus cuniculus

<400> SEQUENCE: 45

Gly Ile Asp Leu Ser Arg Tyr Trp Met Ser
1               5                   10

<210> SEQ ID NO 46
<211> LENGTH: 10
<212> TYPE: PRT
<213> ORGANISM: Oryctolagus cuniculus

<400> SEQUENCE: 46

Gly Ile Asp Leu Ser Asn Tyr Tyr Met Ser
1               5                   10

<210> SEQ ID NO 47
<211> LENGTH: 10
<212> TYPE: PRT
<213> ORGANISM: Oryctolagus cuniculus

<400> SEQUENCE: 47

Gly Ile Asp Leu Ser Arg Tyr Trp Met Ser
1               5                   10

<210> SEQ ID NO 48
<211> LENGTH: 10
<212> TYPE: PRT
<213> ORGANISM: Oryctolagus cuniculus

<400> SEQUENCE: 48

Gly Phe Ser Leu Ser Ser Tyr Tyr Met Ser
1               5                   10

<210> SEQ ID NO 49
<211> LENGTH: 10
<212> TYPE: PRT

<213> ORGANISM: Oryctolagus cuniculus

<400> SEQUENCE: 49

Gly Ile Asp Leu Ser Arg Tyr Trp Met Ser
1               5                   10

<210> SEQ ID NO 50
<211> LENGTH: 10
<212> TYPE: PRT
<213> ORGANISM: Oryctolagus cuniculus

<400> SEQUENCE: 50

Gly Val Asp Leu Asn Thr Tyr Ala Met Gly
1               5                   10

<210> SEQ ID NO 51
<211> LENGTH: 10
<212> TYPE: PRT
<213> ORGANISM: Oryctolagus cuniculus

<400> SEQUENCE: 51

Gly Phe Ser Leu Ser Asn Tyr Trp Met Ser
1               5                   10

<210> SEQ ID NO 52
<211> LENGTH: 10
<212> TYPE: PRT
<213> ORGANISM: Oryctolagus cuniculus

<400> SEQUENCE: 52

Gly Phe Asp Ile Ser Ser Tyr Ser Leu Gln
1               5                   10

<210> SEQ ID NO 53
<211> LENGTH: 10
<212> TYPE: PRT
<213> ORGANISM: Oryctolagus cuniculus

<400> SEQUENCE: 53

Gly Phe Ser Leu Ser Thr Tyr Trp Met Ser
1               5                   10

<210> SEQ ID NO 54
<211> LENGTH: 10
<212> TYPE: PRT
<213> ORGANISM: Oryctolagus cuniculus

<400> SEQUENCE: 54

Gly Phe Ser Leu Thr Thr Tyr Asn Val Ala
1               5                   10

<210> SEQ ID NO 55
<211> LENGTH: 15
<212> TYPE: PRT
<213> ORGANISM: Oryctolagus cuniculus

<400> SEQUENCE: 55

Met Ile Ser Gly Gly Asn Thr Trp Tyr Ala Ser Trp Ala Lys Gly
1               5                   10                  15

<210> SEQ ID NO 56
<211> LENGTH: 16
<212> TYPE: PRT
<213> ORGANISM: Oryctolagus cuniculus

```
<400> SEQUENCE: 56

Ile Ser Ser Thr Thr Ser Asn Thr Phe Tyr Ala Ser Trp Ala Lys Gly
1               5                   10                  15

<210> SEQ ID NO 57
<211> LENGTH: 15
<212> TYPE: PRT
<213> ORGANISM: Oryctolagus cuniculus

<400> SEQUENCE: 57

Met Ile Ser Gly Gly Asn Thr Trp Tyr Ala Ser Trp Ala Lys Gly
1               5                   10                  15

<210> SEQ ID NO 58
<211> LENGTH: 16
<212> TYPE: PRT
<213> ORGANISM: Oryctolagus cuniculus

<400> SEQUENCE: 58

Ile Thr Thr Thr Ser Thr Asn Thr Phe Tyr Ala Ser Trp Ala Lys Gly
1               5                   10                  15

<210> SEQ ID NO 59
<211> LENGTH: 15
<212> TYPE: PRT
<213> ORGANISM: Oryctolagus cuniculus

<400> SEQUENCE: 59

Met Ile Ser Gly Gly Asn Thr Trp Tyr Ala Ser Trp Ala Lys Gly
1               5                   10                  15

<210> SEQ ID NO 60
<211> LENGTH: 16
<212> TYPE: PRT
<213> ORGANISM: Oryctolagus cuniculus

<400> SEQUENCE: 60

Val Ile Leu Gly Ser Gly Thr Thr Tyr Tyr Ala Asn Trp Ala Lys Gly
1               5                   10                  15

<210> SEQ ID NO 61
<211> LENGTH: 15
<212> TYPE: PRT
<213> ORGANISM: Oryctolagus cuniculus

<400> SEQUENCE: 61

Phe Ile Gly Gly Gly Asn Thr Phe Tyr Ala Ser Trp Ala Lys Gly
1               5                   10                  15

<210> SEQ ID NO 62
<211> LENGTH: 16
<212> TYPE: PRT
<213> ORGANISM: Oryctolagus cuniculus

<400> SEQUENCE: 62

Phe Ile Arg Pro Asp Gly Ser Ala His Tyr Ala Thr Trp Ala Lys Gly
1               5                   10                  15

<210> SEQ ID NO 63
<211> LENGTH: 17
<212> TYPE: PRT
<213> ORGANISM: Oryctolagus cuniculus

<400> SEQUENCE: 63
```

```
Met Ile Tyr Gly Asp Ser Asn Asn Lys Phe Tyr Ala Asn Trp Ala Lys
1               5                   10                  15

Gly

<210> SEQ ID NO 64
<211> LENGTH: 16
<212> TYPE: PRT
<213> ORGANISM: Oryctolagus cuniculus

<400> SEQUENCE: 64

Ile Ile Gly Gly Thr Gly Asn Thr His Tyr Thr Thr Trp Ala Lys Gly
1               5                   10                  15

<210> SEQ ID NO 65
<211> LENGTH: 12
<212> TYPE: PRT
<213> ORGANISM: Oryctolagus cuniculus

<400> SEQUENCE: 65

Gly Ile Asp Thr Gly Ile Ala Thr Thr Phe Asn Leu
1               5                   10

<210> SEQ ID NO 66
<211> LENGTH: 12
<212> TYPE: PRT
<213> ORGANISM: Oryctolagus cuniculus

<400> SEQUENCE: 66

Tyr Gly Gly Asn Ser Ala Tyr Tyr Ala Phe Ser Leu
1               5                   10

<210> SEQ ID NO 67
<211> LENGTH: 12
<212> TYPE: PRT
<213> ORGANISM: Oryctolagus cuniculus

<400> SEQUENCE: 67

Gly Ile Asp Thr Gly Ile Ala Thr Thr Phe Asn Leu
1               5                   10

<210> SEQ ID NO 68
<211> LENGTH: 12
<212> TYPE: PRT
<213> ORGANISM: Oryctolagus cuniculus

<400> SEQUENCE: 68

Tyr Gly Gly Asn Ser Ala Tyr Tyr Ala Phe Ser Leu
1               5                   10

<210> SEQ ID NO 69
<211> LENGTH: 12
<212> TYPE: PRT
<213> ORGANISM: Oryctolagus cuniculus

<400> SEQUENCE: 69

Gly Ile Asp Thr Gly Ile Ala Thr Thr Phe Asn Leu
1               5                   10

<210> SEQ ID NO 70
<211> LENGTH: 16
<212> TYPE: PRT
<213> ORGANISM: Oryctolagus cuniculus

<400> SEQUENCE: 70
```

```
Asp Arg Tyr Gly Ser Leu Glu Glu Val Ile Thr Pro Tyr Phe Asp Leu
1               5                   10                  15
```

<210> SEQ ID NO 71
<211> LENGTH: 9
<212> TYPE: PRT
<213> ORGANISM: Oryctolagus cuniculus

<400> SEQUENCE: 71

```
Gly Tyr Gly Ala Pro Gly Tyr Asp Leu
1               5
```

<210> SEQ ID NO 72
<211> LENGTH: 11
<212> TYPE: PRT
<213> ORGANISM: Oryctolagus cuniculus

<400> SEQUENCE: 72

```
Asp Asp Ile Ser Ser Asp Tyr Phe Pro Asn Leu
1               5                   10
```

<210> SEQ ID NO 73
<211> LENGTH: 14
<212> TYPE: PRT
<213> ORGANISM: Oryctolagus cuniculus
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 73

```
Glu Tyr Phe Ala Asp Ser Xaa Xaa Gly Xaa Xaa Phe Gly Ile
1               5                   10
```

<210> SEQ ID NO 74
<211> LENGTH: 13
<212> TYPE: PRT
<213> ORGANISM: Oryctolagus cuniculus
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 74

```
Xaa Xaa Leu Gly Gly Gly Xaa Asp Xaa Asp Phe Asp Ile
1               5                   10
```

<210> SEQ ID NO 75
<211> LENGTH: 13
<212> TYPE: PRT
<213> ORGANISM: Oryctolagus cuniculus

<400> SEQUENCE: 75

```
Gln Ser Ser Gln Ser Val Tyr Asn Asn Asn Arg Leu Ser
1               5                   10
```

<210> SEQ ID NO 76
<211> LENGTH: 13
<212> TYPE: PRT
<213> ORGANISM: Oryctolagus cuniculus

<400> SEQUENCE: 76

Gln Ser Ser Gln Ser Val Tyr Asn Asn Asn Tyr Leu Ala
1               5                   10

<210> SEQ ID NO 77
<211> LENGTH: 13
<212> TYPE: PRT
<213> ORGANISM: Oryctolagus cuniculus

<400> SEQUENCE: 77

Gln Ser Ser Gln Asn Val Tyr Asn Asn Asn Arg Leu Ser
1               5                   10

<210> SEQ ID NO 78
<211> LENGTH: 13
<212> TYPE: PRT
<213> ORGANISM: Oryctolagus cuniculus

<400> SEQUENCE: 78

Gln Ser Ser Gln Ser Val Tyr Asn Asn Asn Tyr Leu Ala
1               5                   10

<210> SEQ ID NO 79
<211> LENGTH: 13
<212> TYPE: PRT
<213> ORGANISM: Oryctolagus cuniculus

<400> SEQUENCE: 79

Gln Ser Ser Gln Ser Val Tyr Ser Asn Asn Arg Leu Ser
1               5                   10

<210> SEQ ID NO 80
<211> LENGTH: 11
<212> TYPE: PRT
<213> ORGANISM: Oryctolagus cuniculus

<400> SEQUENCE: 80

Gln Ala Ser Gln Asn Ile Tyr Asn Asn Leu Ala
1               5                   10

<210> SEQ ID NO 81
<211> LENGTH: 13
<212> TYPE: PRT
<213> ORGANISM: Oryctolagus cuniculus

<400> SEQUENCE: 81

Gln Ala Ser Glu Ser Val Tyr Thr Asn Asn Arg Leu Ser
1               5                   10

<210> SEQ ID NO 82
<211> LENGTH: 13
<212> TYPE: PRT
<213> ORGANISM: Oryctolagus cuniculus

<400> SEQUENCE: 82

Gln Ala Ser Glu Ser Val Tyr Asn Lys Asn Asn Leu Ala
1               5                   10

<210> SEQ ID NO 83
<211> LENGTH: 13

```
<212> TYPE: PRT
<213> ORGANISM: Oryctolagus cuniculus

<400> SEQUENCE: 83

Gln Ser Ser Gln Ser Val Tyr Lys Asn Asn Tyr Leu Ser
1               5                   10

<210> SEQ ID NO 84
<211> LENGTH: 11
<212> TYPE: PRT
<213> ORGANISM: Oryctolagus cuniculus

<400> SEQUENCE: 84

Gln Ala Ser Gln Asn Ile Arg Asn Tyr Leu Ala
1               5                   10

<210> SEQ ID NO 85
<211> LENGTH: 7
<212> TYPE: PRT
<213> ORGANISM: Oryctolagus cuniculus

<400> SEQUENCE: 85

Tyr Ala Ser Thr Leu Ala Ser
1               5

<210> SEQ ID NO 86
<211> LENGTH: 7
<212> TYPE: PRT
<213> ORGANISM: Oryctolagus cuniculus

<400> SEQUENCE: 86

Gly Ala Ser Asn Leu Ala Ser
1               5

<210> SEQ ID NO 87
<211> LENGTH: 7
<212> TYPE: PRT
<213> ORGANISM: Oryctolagus cuniculus

<400> SEQUENCE: 87

Tyr Thr Ser Thr Leu Pro Ser
1               5

<210> SEQ ID NO 88
<211> LENGTH: 7
<212> TYPE: PRT
<213> ORGANISM: Oryctolagus cuniculus

<400> SEQUENCE: 88

Gly Ala Ser Asn Leu Ala Ser
1               5

<210> SEQ ID NO 89
<211> LENGTH: 7
<212> TYPE: PRT
<213> ORGANISM: Oryctolagus cuniculus

<400> SEQUENCE: 89

Tyr Thr Ser Thr Leu Ala Ser
1               5

<210> SEQ ID NO 90
<211> LENGTH: 7
<212> TYPE: PRT
<213> ORGANISM: Oryctolagus cuniculus
```

```
<400> SEQUENCE: 90

Ser Ala Ser Thr Leu Glu Ser
1               5

<210> SEQ ID NO 91
<211> LENGTH: 7
<212> TYPE: PRT
<213> ORGANISM: Oryctolagus cuniculus

<400> SEQUENCE: 91

Tyr Ala Ser Thr Leu Ala Ser
1               5

<210> SEQ ID NO 92
<211> LENGTH: 7
<212> TYPE: PRT
<213> ORGANISM: Oryctolagus cuniculus

<400> SEQUENCE: 92

Asp Ala Ser Asp Leu Ala Ser
1               5

<210> SEQ ID NO 93
<211> LENGTH: 7
<212> TYPE: PRT
<213> ORGANISM: Oryctolagus cuniculus

<400> SEQUENCE: 93

Arg Ala Ser Thr Leu Ala Ser
1               5

<210> SEQ ID NO 94
<211> LENGTH: 7
<212> TYPE: PRT
<213> ORGANISM: Oryctolagus cuniculus

<400> SEQUENCE: 94

Ala Ala Ala Asn Leu Ala Ser
1               5

<210> SEQ ID NO 95
<211> LENGTH: 10
<212> TYPE: PRT
<213> ORGANISM: Oryctolagus cuniculus

<400> SEQUENCE: 95

Gln Gly Tyr Tyr Ser Gly Val Ile Asn Val
1               5                   10

<210> SEQ ID NO 96
<211> LENGTH: 10
<212> TYPE: PRT
<213> ORGANISM: Oryctolagus cuniculus

<400> SEQUENCE: 96

Gln Gly Tyr Tyr Asn Gly Val Ile Phe Val
1               5                   10

<210> SEQ ID NO 97
<211> LENGTH: 10
<212> TYPE: PRT
<213> ORGANISM: Oryctolagus cuniculus

<400> SEQUENCE: 97
```

Gln Gly Tyr Tyr Ser Gly Val Ile Asn Val
1               5                   10

<210> SEQ ID NO 98
<211> LENGTH: 10
<212> TYPE: PRT
<213> ORGANISM: Oryctolagus cuniculus

<400> SEQUENCE: 98

Gln Gly Tyr Tyr Asn Gly Val Ile Phe Val
1               5                   10

<210> SEQ ID NO 99
<211> LENGTH: 10
<212> TYPE: PRT
<213> ORGANISM: Oryctolagus cuniculus

<400> SEQUENCE: 99

Gln Gly Tyr Tyr Ser Gly Val Ile Asn Val
1               5                   10

<210> SEQ ID NO 100
<211> LENGTH: 13
<212> TYPE: PRT
<213> ORGANISM: Oryctolagus cuniculus

<400> SEQUENCE: 100

Gln Ser Ala Tyr Tyr Thr Ser Tyr Ile Asp His Asn Val
1               5                   10

<210> SEQ ID NO 101
<211> LENGTH: 12
<212> TYPE: PRT
<213> ORGANISM: Oryctolagus cuniculus

<400> SEQUENCE: 101

Val Gly Tyr Lys Ser Ser Asp Gly Asp Gly Thr Ala
1               5                   10

<210> SEQ ID NO 102
<211> LENGTH: 10
<212> TYPE: PRT
<213> ORGANISM: Oryctolagus cuniculus

<400> SEQUENCE: 102

Ala Gly Gly Gly Ser Gly Asn Val Tyr Asp
1               5                   10

<210> SEQ ID NO 103
<211> LENGTH: 10
<212> TYPE: PRT
<213> ORGANISM: Oryctolagus cuniculus

<400> SEQUENCE: 103

Gln Gly Tyr Tyr Ser Gly Pro Ile Tyr Val
1               5                   10

<210> SEQ ID NO 104
<211> LENGTH: 12
<212> TYPE: PRT
<213> ORGANISM: Oryctolagus cuniculus

<400> SEQUENCE: 104

Gln Gln Gly Tyr Ser Val Ile Asn Val Asp Asn Ile

```
<210> SEQ ID NO 105
<211> LENGTH: 14
<212> TYPE: PRT
<213> ORGANISM: Artificial Sequence
<220> FEATURE:
<223> OTHER INFORMATION: Peptide linker

<400> SEQUENCE: 105

Glu Gly Lys Ser Ser Gly Ser Gly Ser Glu Ser Lys Val Asp
1               5                   10

<210> SEQ ID NO 106
<211> LENGTH: 18
<212> TYPE: PRT
<213> ORGANISM: Artificial Sequence
<220> FEATURE:
<223> OTHER INFORMATION: Peptide linker

<400> SEQUENCE: 106

Lys Glu Ser Gly Ser Val Ser Ser Glu Gln Leu Ala Gln Phe Arg Ser
1               5                   10                  15

Leu Asp

<210> SEQ ID NO 107
<211> LENGTH: 5
<212> TYPE: PRT
<213> ORGANISM: Artificial Sequence
<220> FEATURE:
<223> OTHER INFORMATION: Peptide linker

<400> SEQUENCE: 107

Gly Gly Gly Gly Ser
1               5
```